United States Patent [19]

Ebinuma et al.

[11] Patent Number: 5,965,791
[45] Date of Patent: Oct. 12, 1999

[54] VECTOR FOR INTRODUCING A GENE INTO A PLANT, AND METHODS FOR PRODUCING TRANSGENIC PLANTS AND MULTITUDINOUSLY INTRODUCING GENES INTO A PLANT USING THE VECTOR

[75] Inventors: Hiroyasu Ebinuma; Koichi Sugita; Etsuko Matsunaga; Mikiko Yamakado, all of Tokyo, Japan

[73] Assignee: Nippon Paper Industries Co., Ltd., Tokyo, Japan

[21] Appl. No.: 08/555,760

[22] Filed: Nov. 9, 1995

[30] Foreign Application Priority Data

| Nov. 9, 1994 | [JP] | Japan | 6-311399 |
| May 31, 1995 | [JP] | Japan | 7-170123 |
| Oct. 4, 1995 | [JP] | Japan | 7-293254 |
| Oct. 25, 1995 | [JP] | Japan | 7-313432 |

[51] Int. Cl.[6] ............ C12N 15/82; C12N 15/29; A01H 5/00; A01H 4/00
[52] U.S. Cl. ............ 800/205; 435/419; 435/172.3; 435/320.1; 536/23.6; 536/24.1
[58] Field of Search ............ 800/205; 435/419, 435/172.3, 320.1; 536/23.6, 24.1

[56] References Cited

U.S. PATENT DOCUMENTS 5,225,341  7/1993  Yoder et al. ............ 435/172.3

FOREIGN PATENT DOCUMENTS

| 0 334 383 | 9/1989 | European Pat. Off. . |
| WO 92/01370 | 2/1992 | WIPO . |
| WO 94/17176 | 8/1994 | WIPO . |

OTHER PUBLICATIONS

Spena et al. Cell–autonomous behavior of the rol/C gene of Agrobacterium rhizogenes during leaf development: a visual assay for transposon excision in transgenic plants. The Plant Cell vol. 1, 1157–1164, Dec. 1989.

James et al. Agrobacterium–mediated transformation of the cultivated strawberry (fragaria x anannassa duch.) using disarmed binary vectors. Plant Sciene, 69 (1990), 79–94.

Dale et al. Gene transfer with subsequent removal of the selection gene from the host genome. Proc. Natl. Acad. Sci. USA. vol. 88, pp.10558–105562, Dec. 1991.

Sandra Holmes Henderson's Dictionary of Biological Terms. Ninth Edition, Van Nostrand Reinhold Company, p. 248, 1979.

Peschke et al. Genetic and molecular analysis of tissue–culture derived Ac elements. Theor. Appl. Genet. (1991) 82: 121–129.

Plant Cell, vol. 1, pp. 1157–1164, 1989, A. Spena, et al., "Cell–autonomous behavior of the rolC gene of Agrobacterium rhizogenes during leaf development: a visual assay for transposon excision in transgenic plants".

*Primary Examiner*—Douglas W. Robinson
*Assistant Examiner*—Thomas Haas
*Attorney, Agent, or Firm*—Oblon, Spivak, McClelland, Maier & Neustadt, P.C.

[57] ABSTRACT

A vector for introducing a desired gene into a planet, which comprises the desired gene and at least one morphological abnormally induction (MAI) gene as a marker gene, or which comprises the desired gene, at least one MAI gene and a removable element. A method for producing a transgenic plant free from the influence of a marker gene. A method for multitudinously introducing desired genes into one plant.

30 Claims, 29 Drawing Sheets

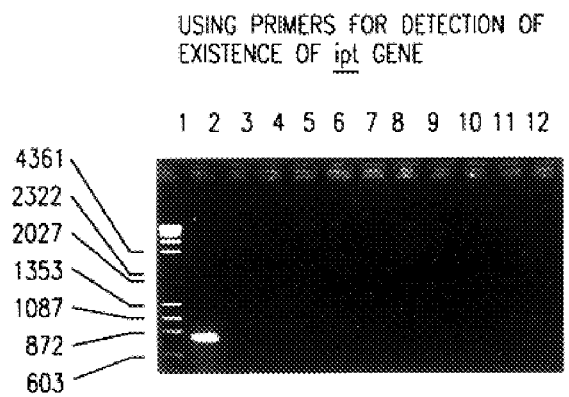

FIG.21

USING PRIMERS FOR DETECTION OF EXISTENCE OF ipt GENE

LANE 1; DNA SIZE MARKER
  λ/*Hind* III - øX174/*Hae* III
  (PRODUCED BY TOYOBO CO., LTD.)
LANE 2; pNPI132 (CONTROL)
LANE 3; LINE NO. 15-NORMAL INDIVIDUAL NO. 1
LANE 4; LINE NO. 15-NORMAL INDIVIDUAL NO. 2
LANE 5; LINE NO. 16-NORMAL INDIVIDUAL NO. 1
LANE 6; LINE NO. 17-NORMAL INDIVIDUAL NO. 1
LANE 7; LINE NO. 18-NORMAL INDIVIDUAL NO. 1
LANE 8; LINE NO. 19-NORMAL INDIVIDUAL NO. 1
LANE 9; LINE NO. 19-NORMAL INDIVIDUAL NO. 2
LANE 10; LINE NO. 20-NORMAL INDIVIDUAL NO. 1
LANE 11; LINE NO. 20-NORMAL INDIVIDUAL NO. 2
LANE 12; LINE NO. 21-NORMAL INDIVIDUAL NO. 1

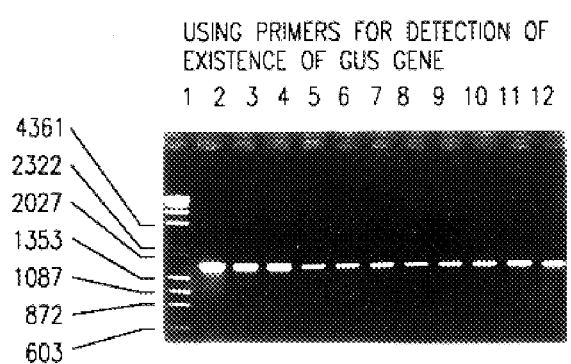

FIG.23

USING PRIMERS FOR DETECTION OF
EXISTENCE OF GUS GENE

LANE 1; DNA SIZE MARKER
  λ/Hind III -øX174 /Hae III
  (PRODUCED BY TOYOBO CO., LTD.)
LANE 2; pNPI132 (CONTROL)
LANE 3; LINE NO. 15-NORMAL INDIVIDUAL NO. 1
LANE 4; LINE NO. 15-NORMAL INDIVIDUAL NO. 2
LANE 5; LINE NO. 16-NORMAL INDIVIDUAL NO. 1
LANE 6; LINE NO. 17-NORMAL INDIVIDUAL NO. 1
LANE 7; LINE NO. 18-NORMAL INDIVIDUAL NO. 1
LANE 8; LINE NO. 19-NORMAL INDIVIDUAL NO. 1
LANE 9; LINE NO. 19-NORMAL INDIVIDUAL NO. 2
LANE 10; LINE NO. 20-NORMAL INDIVIDUAL NO. 1
LANE 11; LINE NO. 20-NORMAL INDIVIDUAL NO. 2
LANE 12; LINE NO. 21-NORMAL INDIVIDUAL NO. 1

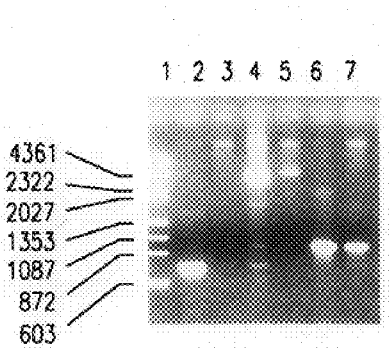

FIG.29

LANE 1; DNA SIZE MARKER
  λ/Hind III - øX174/Hae III
  (PRODUCED BY TOYOBO CO., LTD.)
LANE 2; pNPI140 (CONTROL)
LANE 4; pNPI139 (CONTROL)
LANE 6; pNPI140 (CONTROL)
LANE 3, 5, 7; NORMAL SHOOT AFTER MULTIPLE INTRODUCTION
LANE 2, 3; USING PRIMERS FOR DETECTION OF
  EXISTENCE OF ipt GENE
LANE 4, 5; USING PRIMERS FOR DETECTION OF EXCISION OF THE
  REGION CONTAINING ipt GENE AND HELD BY Rs's
LANE 6, 7; USING PRIMERS FOR DETECTION OF EXISTENCE OF HPT GENE

VECTOR FOR INTRODUCING A GENE INTO A PLANT, AND METHODS FOR PRODUCING TRANSGENIC PLANTS AND MULTITUDINOUSLY INTRODUCING GENES INTO A PLANT USING THE VECTOR

FIELD OF THE INVENTION

The present invention relates to a novel vector for introducing a desired gene into a plant using genetic engineering methods to obtain a transgenic plant; a method for producing a transgenic plant free from the influence of a marker gene using this vector; and a method for introducing at least two desired genes into a plant using this vector.

BACKGROUND OF THE INVENTION

Transformation of microorganisms and cultured cells using genetic engineering is currently applied to the production of physiologically active substances useful as medicines and thus greatly contributes to the industry. In the field of plant breeding, industrial application of genetic engineering lags behind because the life cycles of plants are much longer than those of microorganisms. However, since this technology enables a desired gene to be directly introduced into plants to be bred, it has the following advantages compared to classical breeding which requires multiple crossing.

(a) It is possible to introduce only a characteristic to be improved.

(b) It is possible to introduce characteristics of species other than plants (such microorganisms and the like).

(c) It is possible to greatly shorten the breeding period. Thus engineering methods for plant breeding have been investigated vigorously.

The production of transgenic plants requires the following three steps.

(1) Introducing the desired gene into the plant cell (including introduction of the same into the chromosomes, nucleus and the like).

(2) Selecting plant tissue made only of cells into which the desired gene has been introduced.

(3) Regenerating a plant from the selected plant tissue.

In order to select transgenic tissues into which a desired gene has been introduced, visual identification of the tissue in which the desired gene is expressed without regenerating the new plant has been desired. To achieve this, the desired gene is typically introduced into the plant cell together with a marker gene of which the expression can be easily detected at the stage of cultivating the cell. That is, the expression of the marker gene is used as an index of the introduction of the desired gene. Examples of conventional marker genes include antibiotics-resistant genes, such as kanamycin-resistant gene (i.e., NPTII; neomycin phosphotransferase gene), a hygromycin-resistant gene (i.e., HPT; hygromycin phosphotransferase gene), amino acids synthetase genes, such as a nopaline synthetase gene (NOS), an octopine synthetase gene (OCS), and a sulfonylurea-resistant gene (i.e., ALS; acetoactate synthetase gene) that imparts agricultural chemical resistance.

However, the expression of a marker gene can case serious problems when such a transgenic plant is used for food. That is, it is quite difficult to ensure that a gene product produced by expressing a marker gene is safe for the human body. Consequently, if a transgenic plant containing a marker gene is to be sold as a food, a detailed investigation must be performed to determine the influence of the marker gene on the human body. For example, the NPTII gene has been used as a marker gene at the laboratory level since the early 1980s. In 1994, the product of that gene was finally accepted as a food additive by the U.S. Food and Drug Administration (FDA). Since then, transgenic plants containing the NPTII gene as a marker gene have been used for food. However, some consumers of products containing the NPTII gene are still anxious about this gene's effect.

Moreover, marker gene which are practically used are only genes, such as the NPTII gene, which contribute to detoxification of a growth inhibitory substance in plant cells. Therefore, to select transgenic plant tissue into which a desired gene has been introduced, the tissue is cultivated in a culture medium containing the growth inhibitory substance, and the expression of the marker gene, namely the resistance at the tissue to the growth inhibitory substance is evaluated and used as an index. However, even when a tissue has such a resistance, cultivation in the presence of an inhibitory substance can result in undesirable side effects on the plant cells, such as a decrease in proliferation and redifferentiation of the transgenic tissue.

Further, the expression of a marker gene in a plant cell after the selection of transgenic tissue seriously obstructs plant breeding by subsequent gene introduction. That is, when another gene is introduced into a transgenic plant containing a marker gene, the gene introduction must be monitored using a different marker gene. However, the effectiveness of a marker gene various with the plant species. Therefore, a preliminary test is required to set the conditions for each marker gene (for example, it is reported that the HPT gene is more effective in rice plants than the NPTII gene (K. Shimamoto et al., Nature (London), vol.338, p.274, 1989)). Still further, since the varieties of marker gene are limited, the multiple introduction of a gene cannot be repeated indefinitely simply by changing the marker gene. That is, the number of gene introductions into a certain plant is limited itself by the variety of marker genes which can be used in that plant. Besides, the kind of the marker gene which can be actually used is limited as mentioned above. Accordingly, it is desirable to find a method for removing the marker gene from the chromosome after selection of the transgenic plant tissue to exclude the influence of the marker gene from the cell, tissue and plant.

To eliminate the influence of a marker gene, two methods have been reported. In one method, a marker gene and a transposon of the plant is introduced into a plant chromosome and subsequently removed therefrom following transposon (International Laid-Open No. WO 92/01370). In a second method, the site-specific recombination system of P1 phage is used instead of the transposon (International Laid-Open No. WO 93/01283). Using these methods, it is possible to obtain a cell in which the marker gene has been removed from the plant chromosome at a given ratio after the introduction of the gene. Unfortunately, the probability that the marker gene is removed is very low.

Further, plant cells in which the marker genes have been removed from the chromosomes using these methods are scattered among the cells in which the marker genes are still present and expressed. These two kinds of the cells cannot be distinguished visually.

Plant cells containing marker genes and a desired gene can be selected based on their chemical resistance, nutritional requirements and the like. However, at the time of the selection, the cells lacking marker genes exhibit serious growth inhibition and are destroyed in many cases. Accordingly, these selections cannot be applied to obtain cells lacking marker genes.

In order to obtain plants which lack a marker gene and which contain the desired gene using the above-mentioned methods, the tissue of plant, in which cells lacking the marker gene and cells containing the marker genes are mixed, are proliferated, regenerated, and then analyzed for the selection, using methods such as Southern hybridization or polymerase chain reaction. This method is based on the premise that a regenerated individual is derived from a single cell and therefore all of the plant's cells should have the same characteristics. Thus, an individual derived from a cell lacking the marker gene are made only of such cells. Unfortunately, cells constituting such a regenerated individual are not necessarily uniform. Cells lacking the marker gene chromosome and cells containing the marker gene are coexistent and distributed quite irregularly even in the same individual regenerated plant and in the same tissue thereof. Thus, it is extremely difficult to obtain an individual made only of cells lacking the marker gene at the stage in which the cultured tissue is redifferentiated to regenerate the individual.

In addition, known analytical methods of selection use a tissue, such as a leaf, as a test sample (not a whole individual or a single cell). Consequently, only the overall tendency is analyzed with respect to the state of the marker gene present in one leaf. Besides, in this case, it is common that the marker gene-free cell and the marker gene-containing cell are both present in the same individual or tissue. So, even if an individual made only of cells lacking the marker gene happens to be formed, it is difficult to select this. Even if the presence of the marker gene is not detected in this tissue, tissues in other sites of the same individual may contain the marker gene, or it simply shows that the amount of the marker gene is below the detected limit. Therefore, it is impossible to determine if the test sample is completely free from the marker-gene-containing cells.

Using the above-mentioned methods, an individual lacking the marker gene is obtained only from a germ cell, such as a pollen, an egg cell and the like. When the self-pollination is conducted using the egg cell lacking the marker gene, a fertilized egg lacking the marker gene is obtained at a fixed ratio according to a classical hereditary law, and from this fertilized egg, an individual made only of cells having the same characteristics as the fertilized egg is produced. Conventional analytical methods such as Southern hybridization may be conducted using this individual. Namely, even if the cell lacking the marker gene is produced by the method described in the report referred to here, the individual made only of such a cell is obtained for the first time by redifferentiating the plant from the cultured tissue containing such a cell, conducting crossing of the regenerated plant and obtaining progeny of $F_1$ or later generations. The thus-obtained individual can be selected as an individual lacking the marker gene.

In order to remove the marker gene from the transgenic plant, JP-A-6-276872 reports a technique for gene introduction in which a marker gene is inserted into a separate plasmid vector different from the vector containing the desired gene. The plasmid containing the marker gene is removed from the cell after the completion of the gene introduction (the term "JP-A" as used herein means a Japanese published patent application). However, this technique requires a crossing step for the removal of the marker gene. In this respect, the technique is the same as those of the above-mentioned two reports.

The above methods are difficult to apply to woody plants that have a long growth period, sterile individuals or hybrid individual in which $F_1$ is itself valuable. Further, when removable DNA elements, such as a transposon and the like, are used, the ratio at which these elements are removed from the chromosomal DNA, virus vector DNA and the like where these elements are present and function is typically extremely low. Accordingly, it is necessary that the removal of these elements (namely, the removal of the marker gene) can be easily detected actually at least at the stage of the cultured tissue. When this cannot be detected before redifferentiation of the cultured tissue and the formation of a later generation via the crossing of the regenerated individual, the method is impractical.

SUMMARY OF THE INVENTION

Accordingly, one object of the present invention is to provide a vector containing a gene desired to be introduced into a plant and a marker gene, wherein a plant containing the same has no adverse effect on the human body when ingested, even if the marker gene is expressed.

Another object of the present invention is to provide a vector for introducing a desired gene into a plant, wherein the vector contains a marker gene that enables selection of a transgenic tissue without the use of a plant cell growth inhibitory substance that decreases the activity of the plant cell.

Still another object of the present invention is to provide a vector for introducing a desired gene into a plant, wherein the vector contains a marker gene, and functions to exclude the influence of the marker gene by removing the marker gene from the DNA, where the marker gene is present and functions. Using this vector, a desired gene can be repeatedly introduced efficiently.

A further object of the present invention is to provide a method for producing a transgenic plant using such a vector, which can exclude the influence of the marker gene, without undergoing the step of the production of $F_1$ or later generations by crossing, and a method for multitudinously introducing genes into a plant by applying the above-described method.

These and other objects of the present invention have been achieved using a vector, which comprises a desired gene and at least one morphological abnormality induction (hereinafter referred to as "MAI") gene as a marker gene.

Furthermore, these and other objects of the present invention have been achieved using such a vector, wherein the marker gene is removed from the DNA after its expression. Expression of the marker gene and the disappearance of the function thereof are detectable by morphological changes in the tissue into which the marker gene has been introduced.

Moreover, these and other objects of the present invention have been achieved using a vector which comprises a desired gene, at least one MAI gene as a marker gene, and a removable DNA element. The MAI gene is positioned such that it behaves integrally with the removable DNA element. The desired gene is positioned such that it does not behave integrally with the removable DNA element.

Still furthermore, these and other objects of the present invention have been achieved by a method for producing a transgenic plant free from the influence of a marker gene, which comprises the following steps:

(A) introducing a vector into a plant cell, wherein said vector comprises a desired gene, at least one MAI gene as a marker gene, and a removable DNA element, wherein said MAI gene is positioned such that it behaves integrally with the removable DNA element, and wherein said desired gene is positioned such that it does not behave integrally with the removable DNA element, (B) cultivating the plant cell obtained in (A), detecting a morphologically abnormal plant tissue which appears during the cultivation, and selecting said morphologically abnormal tissue, and (C) cultivating said morphologically abnormal tissue selected in (B), detecting a morphologically normal tissue which appears during the cultivation, and selecting said morphologically normal tissue.

Still moreover, these and other objects of the present invention have been achieved by a method for introducing at least two desired genes into a plant, which comprises conducting the following steps at least two times:

(A) introducing a vector into a plant cell, wherein said vector comprises a desired gene, at least one MAI gene as a marker gene, and a removable DNA element, wherein said MAI gene is positioned such that it behaves integrally with the removable DNA element, and wherein said desired gene is positioned such that it does not behave integrally with the removable DNA element, (B) cultivating the plant cell obtained in (A), detecting a morphologically abnormal plant tissue which appears during the cultivation, and selecting said morphologically abnormal tissue, and (C) cultivating said morphologically abnormal tissue selected in (B), detecting a morphologically normal tissue which appears during the cultivation, and selecting said morphologically normal tissue.

Additionally, these and other objects of the present invention have been achieved by a plant regenerated by cultivating the above-described morphologically normal tissue.

BRIEF EXPLANATION OF THE DRAWINGS

FIG. 21 is the results of the PCR analysis of normal individuals obtained from shoots Nos. 15 to 21 in Example 5 using primers in which the existence of an ipt gene was detected.

FIG. 23 is the results of the PCR analysis of normal individuals obtained from shoots Nos. 15 to 21 in Example 5 using primers in which the existence of a GUS gene was detected.

FIG. 29 is the results of the PCR analysis of a normal shoot differentiated from an extreme shooty phenotype after multitudinously introduction of genes in Example 8.

DETAILED DESCRIPTION OF THE INVENTION

Figure 1:
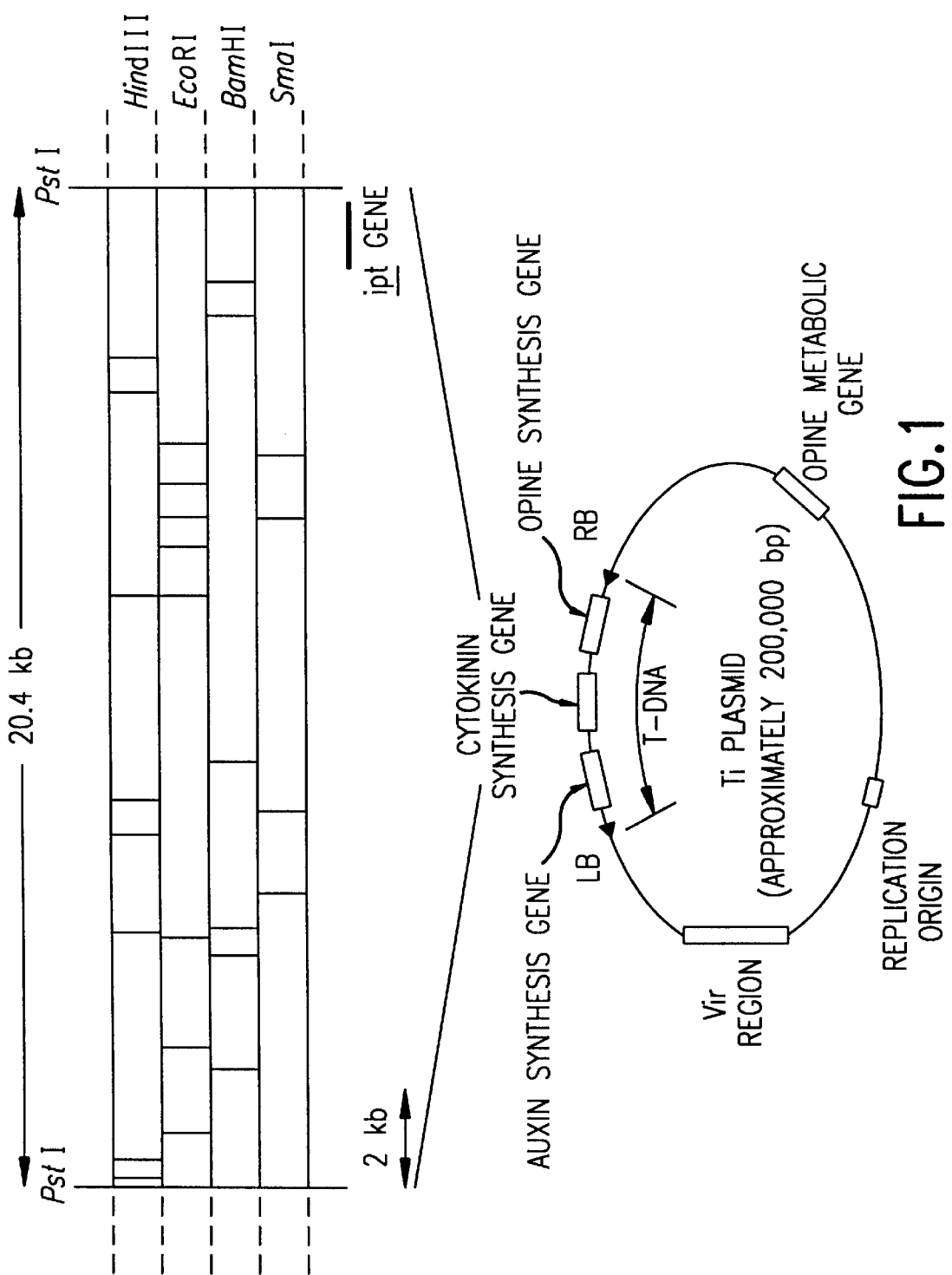
FIG. 1 is a diagram of the Ti plasmid and a restriction endonuclease map of Pst I fragment on a T-DNA region of A. tumefaciens strain PO22.

As used therein, the MAI gene is a gene that induces into a tissue of a plant morphologically abnormal differentiation such as a dwarf, destruction of apical dominance, change in pigments, formation of a crown gall, formation of hairy roots, waving of the leaves or the like. With respect to preferred MAI gene, those genes isolated from bacteria of the genus Agrobacterium or the like that induce tumor or teratoma (e.g., formation of adventitious shoots and adventitious roots) in various plants can be used. Examples of these various MAI genes include cytokinin synthesis genes (e.g., ipt (isopentenyltransferase) gene (A. C. Smigocki, L. D. Owens, *Prod. Natl. Acad. Sci. U.S.A.*, vol.85, p.5131, 1988)), iaaM (tryptophan monooxygenase) gene (H. J. Klee et al., *GENES & DEVELOPMENT*, vol.1, p.86, 1987), gene 5 (H. Körber et al., *EMBO Journal*, vol.10, p.3983, 1991), gene 6b (P. J. J. Hoyaas et al., *Plant Mol. Biol.*, vol. 11, p.791, 1988), and rol genes such as rolA, rolB, rolC, and rolD (F. F. White et al., *J. Bacteriol.*, vol.164, p.33, 1985). Furthermore, examples thereof include an iaaL (indoleacetic acid-lysine synthetase) gene as *Pseudomonas syringae* subsp. savastanoi (A. Spena et al., *Mol. Gen. Genet.*, vol.227, p.205, 1991), homeo box genes and phytochrome genes in various plants. Prefereably, the cytokinin synthesis genes such as the ipt gene or at least one gene selected from the rol genes (more preferably, rol genes containing genes rolA, rolB and rolC) are used. The ipt gene is present in the T-DNA of *Agrobacterium tumefaciens* and induces destruction of apical dominance. The rol genes containing genes rolA, rolB and rolC are present in the T-DNA of *Agrobac-*

*terium rhizogenes* and at least one these induces the formation of hairy roots, dwarf, waving of the leaves and the like of a plant regenerated from the hairy root.

Using the techniques of the present invention, one can design a combination of these marker genes, so that a specific structure, such as an adventitious shoot, an adventitious root or the like is redifferentiated in a specific plant into which these marker genes are introduced. In the present invention, such a combination of MAI genes can be used, according to the conditions of producing the transgenic plant, such as the kind of a plant into which the genes are to be introduced.

The morphologically abnormal tissue produced by introducing the MAI gene into the cell is made up only of the cells containing this gene. Therefore, using this gene as the marker gene, a vector is constructed together with the desired gene. When this vector is introduced into the plant cell and the transgenic cell is cultivated, the tissue made up only of this cell into which the marker gene and the desired gene are introduced can be selected by visually selecting the morphologically abnormal tissue formed from this cell.

Suitable vectors useful in accordance with the present invention have a DNA sequence which introduces a foreign gene into a host cell and which expresses the foreign gene within a cell of a host.

When the gene is introduced using the vector of the present invention, the plant tissue made up only of the transformed cell can be visually selected by merely cultivating the cell after the operation for the gene introduction in a common culture medium such as MS (Murashige-Skoog) culture medium under ordinary cultivation conditions. Since there is no need to use a special substance for selecting the transformed tissue, such as a plant cell growth inhibitory substance or the like, not only is the procedure simplified, but also the activity of the plant cell is not decreased through such a substance. In addition, the plant has inherently the MAI gene, or the MAI gene is spontaneously introduced into the plant through infection with bacteria or the like. Accordingly, a plant obtained using the vector of the present invention is no different from naturally occurring plants which have this morphologic abnormality.

Suitable vectors in accordance with the present invention include a vector where the MAI gene is positioned such that it behaves integrally with a removable DNA element and the desired gene is positioned such that it does not behave integrally with the removable DNA element.

As used herein, a removable DNA element is an element of a DNA sequence which itself is removable from the DNA wherein the DNA element exists and functions. In plants, a transposon present in a chromosome is known as this element. The structure, activity and behavior of transposons have been almost completely identified. For the transposon to function, two components are required in principle, (1) an enzyme which is expressed from the gene present therein and which catalyzes the excision and transposition of the transposon itself (transposase) and (2) DNA binding sequences which are present in the terminal region of the transposon and upon which the transposase acts. By these elements, the transposon is excised from the chromosome in which it exists, and is then usually transposed to a new position in the DNA. However, at a certain ratio, the transposon also disappears without being transposed. The present invention makes use of such a transposition error of the transposon.

The transposon can be of one of two types, either an autonomous transposon or a non-autonomous transposon. The autonomous transposon maintains the two elements, the transposase and the DNA binding sequence. In the autonomous transposon, the transposase is expressed and binds to the DNA binding sequence for action, whereby the transposon is autonomously excised from the chromosome. The non-autonomous transposon retains the terminal DNA binding sequence to which the transposase is bound for action. In the non-autonomous transposon, the transposase gene undergoes mutation such that the transposase is not expressed; thus the transposon cannot be excised from the chromosome autonomously. However, when transposase is supplied to the non-autonomous transposon from the autonomous transposon or from an independent transposase gene, the non-autonomous transposon behaves similarly to the autonomous transposon.

Examples of the autonomous transposons include Ac and Spm isolated from maize (A. Gieri and H. Saedler, *Plant Mol. Biol.*, vol.19, p.39, 1992). Ac can be obtained by digesting wx-m7 gene locus in the chromosome of the maize with restriction endonuclease Sau3A (U. Behrens et al., *Mol. Gen. Genet.*, vol.194, p.346, 1984). This autonomous transposon is the most analyzed among plant transposons. In fact, the DNA sequence has already been determined (M. Müller-Neumann et al., *Mol. Gen. Genet.*, vol.198, p.19, 1984).

Examples of non-autonomous transposons include Ds and dSpm obtained by deleting the inner regions of Ac and Spm, respectively (H. -P. Doring and P. Starlinger, *Ann. Rev. Genet.*, vol.20, p.175, 1986) and those isolated from many plants, other than maize, such as snapdragon, morning glory and the like (for example, Y. Inagaki et al., *Plant Cell*, vol.6, p.375, 1994). When these transposons are introduced into chromosomes of exogenous plants, these transposons are also excised from a chromosome and transposed upon exhibiting the activity (for example, B. Baker et al., *Proc. Natl. Acad. Sci. U.S.A.*, vol.83, p.4844, 1986).

In the present invention, both the autonomous and non-autonomous transposons can be used. The non-autonomous transposon may be used upon inserting thereinto a functioning transposase gene.

Another removable DNA element, which is not present in plants, but which can be used in accordance with the present invention is an element derived from a site-specific recombination system. A site-specific recombination system consists of two elements, (1) a recombination site (corresponding to the removable DNA element of the present invention) having a characteristic DNA sequence, and (2) an enzyme that binds to the DNA sequence specifically and catalyzes the recombination between DNA sequences if two or more of the sequences exist (recombinase). When the two DNA sequences are oriented in the same direction at a given interval on the same DNA molecule, the region held by these DNA sequences is excised from the DNA molecule, such as a plasmid, chromosome or the like. When the two DNA sequences are oriented in opposite directions on the same DNA molecule, the region held by these DNA sequences is inverted.

The present invention preferably utilizes the former excision. Both excision and inversion within the recombination site occur as a result of homologous recombination through the site-specific recombination system, which is different from the mechanism using the transposon. It is known that the recombinase gene is not necessarily present in the same DNA molecule, in which the recombination site exist. The recombinase gene only needs to be present in the same cell and expressed to excise or invert the region held by the two DNA sequences (N. L. Craig, *Annu. Rev. Genet.*, vol.22, p.77, 1988).

At present, site-specific recombination systems have been identified in microorganisms such as phage, bacterium (e.g., *E. coli*), yeast and the like. Examples thereof include a Cre/lox system, a pSR1 system, a FLP system, a cer system, and a fim system (for example, N. L. Craig, *Annu. Rev. Genet.*, vol.22, p.17, 1988). When the site-specific recombination system separated from these microorganisms with the use of a Cre/lox system derived from P1 phage (WO 93/01283) is introduced into organisms (including plants) different from the organism from which this system had been derived, it behaves in the same way as in the original organism. The site-specific recombination system of yeast (*Zygosaccharomyces rouxii*) (pSR1 system (H. Matsuzaki et al., *J. Bacteriology*, vol.172, p.610, 1990)) can also be used in accordance with the present invention. This pSR1 system also maintains its inherent function in higher plants (H. Onouchi et al., *Nucleic Acid Res.*, vol.19, p.6373, 1991).

In the present invention, the morphological abnormality induction (MAI) gene may be inserted into a position where this gene is excised along with the removable DNA element. For instance, when the transposon is used as the removable DNA element, the MAI gene can be inserted into a position which does not influence the excision of the transposon and which is upstream of the promoter region of the transposase gene but downstream of the terminal region to which the transposase binds. When the pSR1 system is used, the MAI gene can be inserted into any position within the region held by the characteristic DNA sequences which does not inhibit the expression of the recombinase.

In the present invention, the MAI gene is preferably present within the removable DNA element. On the other hand, the position of the desired gene is not particularly limited; however, preferably, the desired gene is present outside of the removable DNA element.

Using the vector of such a structure after the desired gene introduction, the MAI gene can be removed at a certain frequency, along with the removable DNA element, from the DNA in which it is introduced and functions. The desired gene which does not behave integrally with the marker gene remains in the same DNA. The vector can be used to multiply introduce a desired gene into a certain plant. In addition, since the loss of the function of this MAI gene can be visually detected as a morphological change of the transgenic tissue during cultivation, the tissue made up only of the cell with the desired gene but without the marker gene can be selected with ease and without the need for a special procedure. Consequently, even when such a cell is actually formed at a low ratio, the cell can be sufficiently selected to make the procedure practically useful. Further, not only can the multiple introduction of the gene using this vector be repeated many times, but this can be repeated before a mature plant is regenerated. Thus, multiple introduction can be conducted efficiently. In order to obtain the individual transgenic plant made up only of such cells, the plant may be regenerated from the thus-selected tissue without having to undergo the crossing step. The thus-obtained individual transgenic plant is completely free from any adverse effects on the human body caused by the marker gene as mentioned above. Moreover, the use of this vector does not require a cell growth inhibitory substance that might decrease the activity of the cell in the step of selecting the transgenic tissue.

The vector of the present invention can be used in any plants into which the gene can be introduced by genetic engineering methods. The desired gene in accordance with the present invention can be any gene by which agriculturally excellent characteristics can be imparted and any gene which allows for studies of gene expression mechanisms and the like, though agriculturally excellent characteristics are not necessarily imparted.

For producing a protein such as enzyme from a gene, a structural gene sequence encoding information of the polypeptide and regulatory sequences of the structural gene, such as a promoter sequence (expression initiation sequence), a terminator sequence (expression termination sequence) and the like, are generally required. Examples of suitable promoter sequence that functions in the plant include the 35S promoter of a cauliflower mosaic virus (J. T. Odell et al., *Nature* (London), vol.313, p.810, 1985), the promoter of a nopaline synthetase (W. H. R. Langridge et al., *Plant Cell Rep.*, vol.4, p.355, 1985), and the promoter of ribulose diphosphate carboxylase/oxygenase small subunit (R. Fluher et al., *Proc. Natl. Acad. Sci. U.S.A.*, vol.83, p.2358, 1986). Examples of suitable terminator sequence include the polyadenylation signal of a nopaline synthetase (A. Depicker et al., *J. Mol. Appl. Gen.*, vol.1, p.561, 1982) and the polyadenylation signal of an octopine synthetase (J. Gielen et al., *EMBO J.*, vol.3, p.835, 1984). Accordingly, when necessary, a gene on the vector of the present invention comprises a structural gene and the gene expression regulatory sequences thereof. The gene, or gene and regulatory sequences, can be obtained by chemical synthesis or by cloning cDNA or genomic DNA.

The vector of the present invention can be indirectly introduced into the plant cell through viruses or bacteria with which plants are infected (I. Potrykus, *Annu. Rev. Plant Physiol. Plant Mol. Biol.*, vol.42, p.205, 1991). Examples of suitable viruses include cauliflower mosaic virus, geminivirus, tobacco mosaic virus and brome mosaic virus. Examples of suitable bacteria include *Agrobacterium tumefaciens* (hereinafter referred to as *A. tumefaciens*), and *Agrobacterium rhizogenes* (hereinafter referred to as *A. rhizogenes*). Dicotyledonous plants are generally known to be infected with the bacteria of the genus Agrobacterium. Recently, the introduction of genes into the monocotyledonous plants by the infection of these plants with them has also been reported (for example, in International Laid-Open No. WO 94/00977).

The vector of the present invention can be directly introduced into the plant cell by physical and chemical methods such as a microinjection, an electroporation, a polyethylene glycol method, a fusion method and a high-speed ballistic penetration (I. Potrykus, *Annu. Rev. Plant Physiol. Plant Mol. Biol.*, vol.42, p.205, 1991). Since the general indirect introduction method using the genus Agrobacterium cannot be applied to many of the monocotyledonous plants and the dicotyledonous plants which are resistant to infection with Agrobacterium, the above-mentioned direct introductioin methods are effective for these plants.

The vector for use in the present invention is not particularly limited as long as the requirements of the present invention are satisfied. For example, if the vector is indirectly introduced into the plant cell, the vector may be a Ti vector or a virus vector. Examples of the Ti vector for use in the present invention include Bin19 (M. Bevan et al., *Nucleic Acids Res.*, vol.12, p.8771, 1984), pRAL3940 (A. Hoekema et al., *Plant Mol. Biol.*, vol.5, p.85, 1985), pGA492 and pGA482 (G. An et al., *Plant Physiol.*, vol.81, p.86, 1986), pL22 (C. Simoens et al., *Nucleic Acids Res.*, vol.14, p.8075, 1986), pAGS111 (P. Van den Elzen et al., *Plant Mol. Biol.*, p.5, vol.149, 1985), pEND4K (H. J. Klee et al., *Bio/Technology*, vol.3, p.637, 1985), pGV831 (R. De Blaere et al., *Nucleic Acids Res.*, vol.13, p.4777, 1985), and pMON200 (R. T. Fraley et al., *Bio/Technology*, vol.3, p.629, 1985). Examples of the virus vector for use in the present invention include cauliflower mosaic virus vector (N. Brisson et al., *Nature* (London), vol.310, p.511, 1984), geminivirus vector (R. J. Hayes et al., *Nature* (London), vol.334, p.179, 1988), brome mosaic virus vector (R. French et al., *Science* (vol.231, p.1294, 1986), tobacco mosaic virus vector (N. Takamatsu et al., *EMBO J.*, vol.6, p.307, 1987), and agroinfection vector (N. Grimsley et al., *Nature* (London), vol.325, p.177, 1987). However, the vectors for use in the present invention are not limited thereto.

Furthermore, the desired gene for use in the present invention is not particularly limited. The nature of the desired gene itself is not critical to the present invention. Examples of the desired gene for use in the present invention include genes for disease resistance (e.g., gene for endotoxin of *Bacillus thuringiensis*, WO 92/20802)), herbicide resistance (mutant acetolactate synthase gene, WO 92/08794)), seed storage protein (e.g., glutelin gene, WO 93/18643)), fatty acid synthesis (e.g., acyl-ACP thioesterase gene, WO 92/20236)), cell wall hydrolysis (e.g., polygalacturonase gene (D. Grierson et al., *Nucl. Acids Res.*, vol.14, p.8595, 1986)), anthocyanin biosynthesis (e.g., chalcone synthase gene (H. J. Reif et al., *Mol. Gen. Genet.*, vol.199, p.208, 1985)), ethylene biosynthesis (e.g., ACC oxidase gene (A. Slater et al., *Plant Mol. Biol.*, vol.5, p.137, 1985)), active oxygen-scavenging system (e.g., glutathione reductase gene (S. Greer & R. N. Perham, *Biochemistry*, vol.25, p.2736, 1986)), and lignin biosynthesis (e.g., phenylalanine ammonia-lyase gene, cinnamyl alcohol dehydrogenase gene, o-methyltransferase gene, cinnamate 4-hydroxylase gene, 4-coumarate-CoA ligase gene, cinnamoyl CoA reductase gene (A. M. Boudet et al., *New Phytol.*, vol.129, p.203, 1995)). However, the desired genes for use in the present invention are not limited thereto.

Moreover, the host plant for use in the present invention is not particularly limited. Examples of herbaceous plant used as the host plant include tobacco (Tabacum), tomato (Lycopersicom), sweet potato (Impoea), potato (Solanum), carrot (Dacus), lettuce (Lactuca), cauliflower (Brassica), cabbage (Brassica), oilseed rape (Brassica), sunflower (Helianthus), sugar best (Bela), asparagus (Asparagus), banana (Musa), cotton (Gossypium), arabidopsis (Arabidopsis), alfalfa (Medicago), peas (Pisum), soybean (Glycine), rice (Oryza), corn (Zea),and rye (Secale). Examples of arboreous plant used as the host plant include poplar (Populus), eucalypti (Eucalyptus), acacia (Acacia), pear (Pyrus), apple (Malus), grape (Vitis), walnut (Juglans), plum (Prunus), rose (Rosa), and spruce (Picea). However, the host plants for use in the present invention are not limited thereto.

In the present invention, the MAI gene is expressed to make the inside of the cell physiological abnormal. Physiological abnormalities include the production of plant growth hormone in a plant cell, with the result that the proliferation and differentiation of the cell containing the MAI gene are confused to induce various morphological abnormalities. For example, an aggregate of disordered shoots with the apical dominance destroyed (extreme shooty phenotype; ESP), hairy roots or the like, can be derived from a cell into which such an MAI gene is introduced. This phenotype is formed by abnormal proliferation and differentiation of the above-mentioned cell. Thus, this morphologically abnormal tissue is made up only of the cell containing this gene. Accordingly, if the vector is constructed using this gene as the marker gene together with the desired gene and is introduced into the plant cell and the cell is cultivated, the tissue made only of the cell into which the marker gene and the desired gene have been introduced can be selected by merely visually selecting the morphologically abnormal tissue formed from the plant cell. Thus, it is possible to visually select the transgenic tissue without conducting any special procedures such as the addition of the plant cell growth inhibitory substance and the like to a culture medium.

Whereas conventional marker genes, such as NPTII gene, are not introduced into plants without genetic engineering; the MAI gene of the present invention is a gene which plants inherently retain or which is naturally introduced into plants by infection with bacteria or the like. For this reason, the safety of that gene product to the human body is considered to be quite high.

Further, in the present invention, the MAI gene is inserted into a position such that it behaves integrally with the removable DNA element. After the vector having such a structure is introduced into the plant, the MAI gene used as the marker gene is removed from DNA along with the removable DNA element at a fixed frequency resulting in the loss of its function. Meanwhile, the desired gene which does not behave integrally with the removable DNA element remains in the same DNA and maintains its function. So, the expression of the same marker gene can be used as an index for the introduction of a desired gene again and again. Accordingly, this vector causes the multiple introduction of the gene into a certain plant by merely changing the structure related to the desired gene to be introduced without imposing any change on the structures of the marker gene and the others. For this reason, the vector can be repetitively used for an unlimited amount of times.

Since the loss of the function of the marker gene, that is, the loss of the function of the MAI gene, can be visually detected, the tissue made up cells lacking the marker gene and containing the desired gene can be obtained surely and easily. That is, the cultivation, the visual selection and the separation may be repeated without the need for any special procedure to obtain such a tissue. Further, the plant made up only of the above-mentioned cell can be obtained by only regenerating the plant from the obtained tissue, without having to undergo the crossing step. Still further, although a transposon is hard to completely remove from DNA because this element has a high transposability, the invention can be sufficiently put to practical use because the selection i s highly efficient.

EXAMPLES

The present invention will be illustrated by referring to the following Examples, but the present invention should not be construed as being limited thereto.

In the following Examples, the experiments were conducted according to the instructions of *Molecular Cloning*, 2nd edition (Sambrook et al. eds., *Cold Spring Harbor Laboratory Press*, New York, 1989) or through a manufacturer unless otherwise instructed.

Example 1
I. Construction of a vector

An ipt gene present in T-DNA of pathogenic *A. tumefaciens* strain PO22 (H. Wabiko, *Chemical Regulation of Plants*, vol.24, p.35, 1989 (see FIG. 1)) was cut out with restriction endonuclease PstI, and plasmid pIPT1 was obtained by ligating the ipt gene into the PstI restriction endonuclease side of plasmid pUC7 (*Molecular Cloning*, 2nd edition, vol. 1, 4.10). From this plasmid, an ipt gene containing a native promoter and a native polyadenylation signal was cut out with restriction endonucleases BamHI and PstI, and plasmid pIPT2 was obtained by ligating the ipt gene into the BamHI-PstI restriction endonuclease sites of plasmid pUC119 (obtained from Takara Shuzo Co., Ltd.). From this plasmid, the structural gene and the native polyadenylation signal of the ipt gene were cut out with restriction endonuclease RsaI, and plasmid pIPT3 was obtained by ligating the ipt gene into the SmaI restriction endonuclease site of plasmid pUC119. Further, the ipt gene inserted into pIPT3 was cut out with restriction endonculeases BamHI and SacI, and plasmid pIPT4 was obtained by ligating the fragment into the BamHI-SacI restriction endonuclease sites of vector plasmid pBI121 (obtained from Clontech Co.) which is useful for the gene introduction into a plant. When a plant is infected with *A. tumefaciens* having the plasmid pIPT4, a T-DNA region which exists between an LB site and an RB site, here a region of approximately 5 kb having the NPTII gene and the ipt gene, comes to be integrated into the chromosome of the plant.

This plasmid pIPT4 was introduced into *E. coli* (*Escherichia coli*) JM109 strain, and it was deposited in accordance with the Budapest Treaty as *E. coli* JM109 (pIPT4) under Deposit No. FERM BP-5063.

Figure 2:
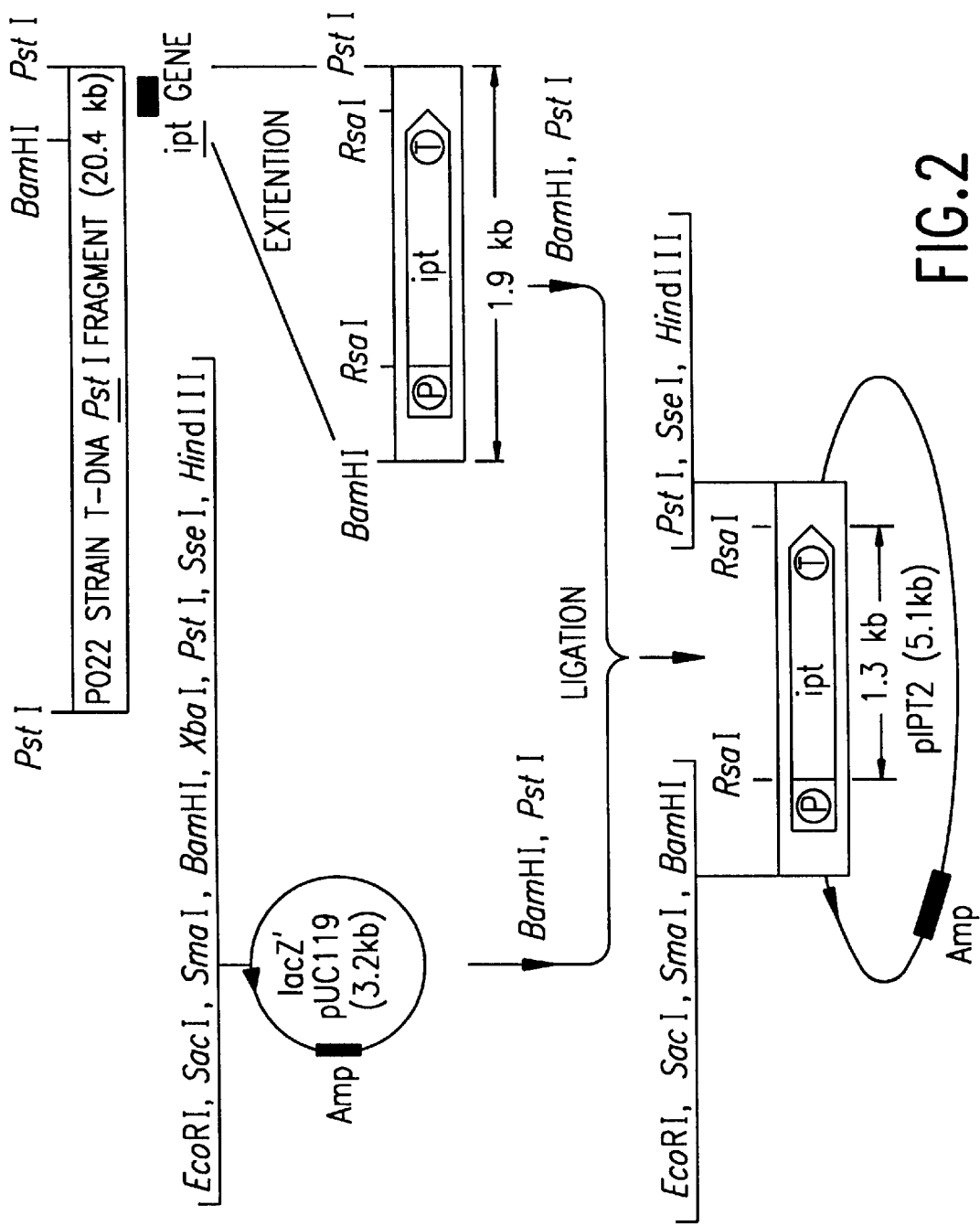
FIG. 2 is a diagram of the construction of pIPT2.
Figure 3:
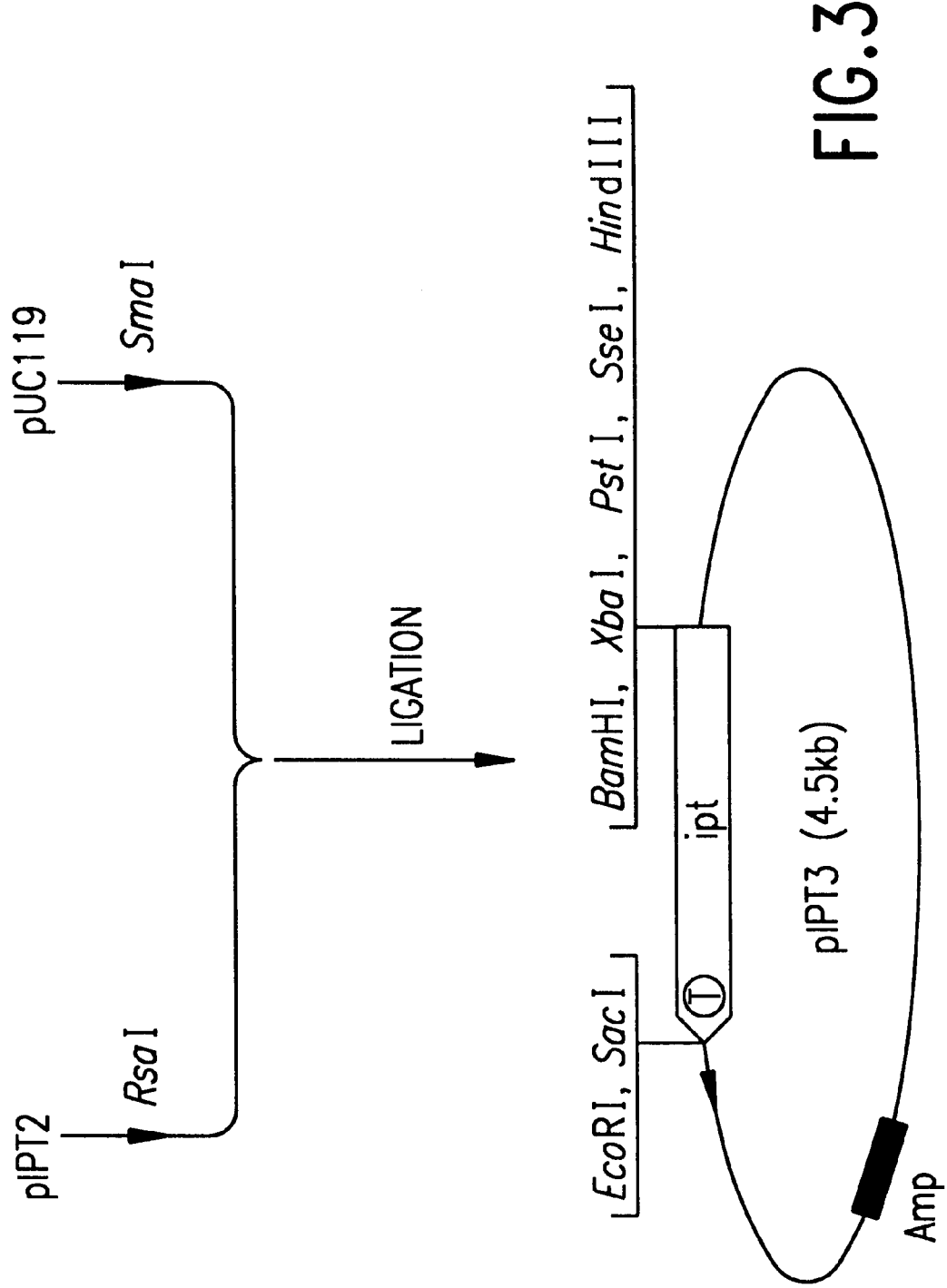
FIG. 3 is a diagram of the construction of pIPT3 from pIPT2.
Figure 4:
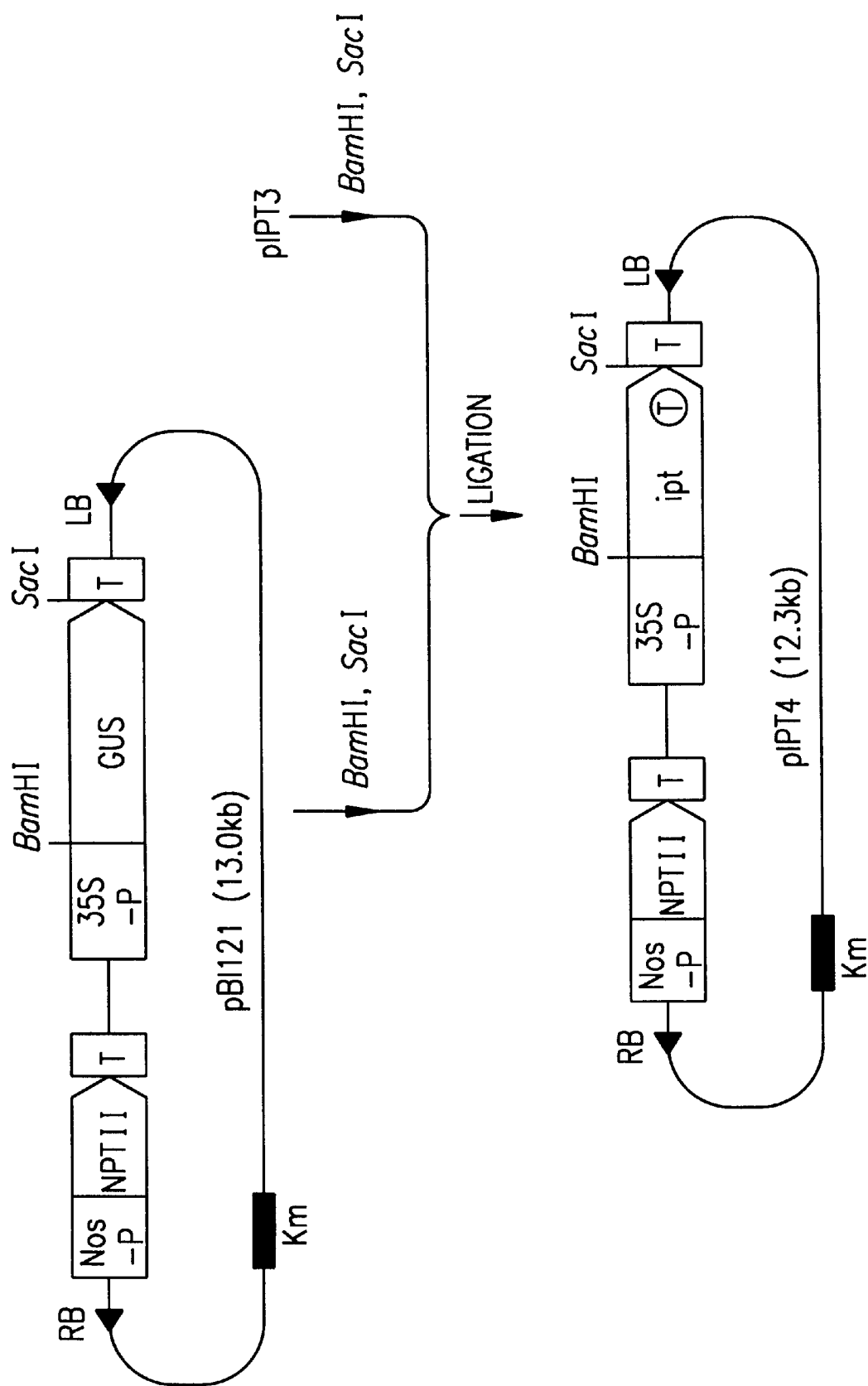
FIG. 4 is a diagram of the construction of pIPT4 from pIPT3.
Figure 5:
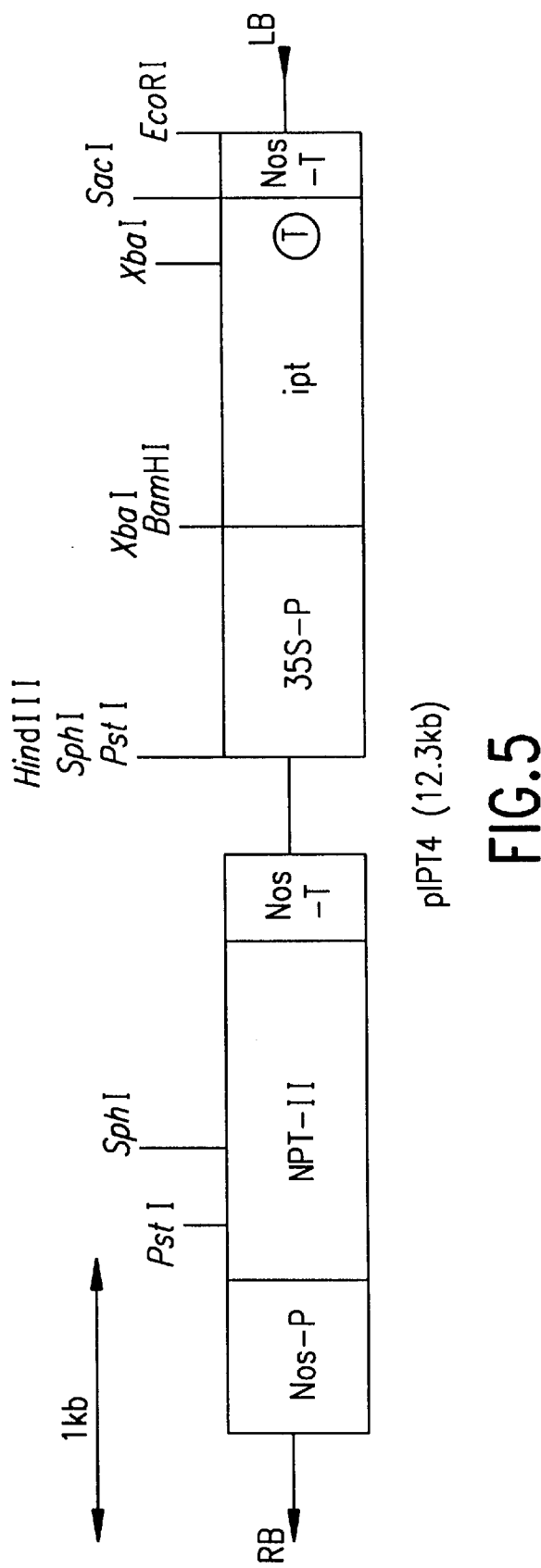
FIG. 5 is the restriction endonuclease map of a T-DNA region in the structure of pIPT4.

The strategy for constructing the plasmid pIPT4 is schematically shown in FIGS. 2 to 4. The restriction endonuclease map of the T-DNA region thereof is shown in FIG. 5. In FIGS. 2 to 4 and 5, encircled "P" and "T" indicate a native promoter and a native polyadenylation signal of the ipt gene itself respectively. 35S-P indicates a 35S promoter of a cauliflower mosaic virus, and Nos-P indicates a promoter of a nopaline synthetase gene. T (FIG. 4) or Nos-T (FIG. 5) indicates a polyadenylation signal of the nopaline synthetase gene.

In this Example, as shown in FIG. 5, for the MAI gene as the marker gene, the ipt gene which contributes to formation of an ESP by inducing the destruction of apical dominance was used, and the NPTII gene was used as a model of the desired gene. The ipt gene is a member of oncogenes that pathogenic *A. tumefaciens* retains. A plant cell into which this ipt gene is introduced causes differentiation which is led to the formation of an ESP through the overproduction of cytokinin, which is a plant hormone.

In this Example, 35S promoter of a cauliflower mosaic virus was used for a promoter sequence of the ipt gene, and the native polyadenylation signal of the ipt gene itself was used for a terminator sequence.

II. Introduction of pIPT4 into Agrobacterium

*A. tumefaciens* strain LBA4404 (obtained from Clontech Co.) was inoculated into 10 ml of YEB liquid culture medium containing 5 g/liter of beef extract, 1 g/liter of yeast extract, 1 g/liter of peptone, 5 g/liter of sucrose, and 2-mM MgSO$_4$, pH of 7.2 at 22° C. (the pH at 22° C. is applied to the following unless otherwise instructed)), and was cultivated at 28° C. until OD$_{630}$ was within the range of from 0.4 to 0.6. Then, the culture was centrifuged at 6,900×g for 10 minutes at 4° C. to collect the cells. The cells were suspended in 20 ml of 10-mM Tris-HCl (pH 8.0), and the suspension was recentrifuged at 6,900×g for 10 minutes at 4° C. Subsequently, the collected cells were resuspended in 200 µl of YEB liquid culture medium, and this suspension was used as a cell solution for introducing a plasmid.

In a 15-milliliter tube (made by Falcon), 200 µl of the cell solution for introducing the plasmid were mixed with 6 µg of plasmid pIPT4 obtained in the above-described step I, and the mixture was cooled by dipping it for 5 minutes in ethanol which had been cooled in liquid nitrogen for from 30 to 40 minutes. The thus-cooled solution, together with the tube, was allowed to stand in a water bath of 29° C. for 25 minutes. Then, 750 µl of YEP liquid culture medium were added thereto, and the mixed solution was cultivated at 29° C. for 1 hour while being shaken. This cell solution was spread on YEB agar culture medium (containing 1.2 w/v % agar and the same ingredients as those of the above-mentioned culture medium) to which 50 mg/liter of kanamycin were added, and cultivated at 28° C. for 2 days. The thus-obtained cell colonies were inoculated into YEB liquid culture medium and further cultivated. Thereafter, the plasmid was extracted from the cells by an alkali method, and cleaved with restriction endonucleases PstI, BamHI and EcoRI. The thus-obtained fragments of the plasmid were analyzed by agarose gel electrophoresis, and it was confirmed that the plasmid pIPT4 was introduced into *A. tumefaciens* strain LBA4404.

III. Introduction of pIPT4 from Agrobacterium into a tobacco matured leaves of a tobacco (*Nicotiana tabacum* cv. xanthi, hereinafter a tobacco means this variety unless otherwise indicated) grown in a greenhouse were dipped in a 1 v/v % sodium hypochlorite aqueous solution for sterilization, and washed three times with sterile water. Then, the midrib of the leaf was removed to form leaf discs of approximately 8 mm square. The thus-obtained leaf discs were then dipped for approximately 1 minute in a cell suspension of *A. tumefaciens* strain LBA4404 introduced pIPT4 in the above-described step II, and was infected therewith (which suspension was diluted with a sterilized water at OD$_{630}$=0.25 after the overnight cultivation in YEB liquid culture medium), and was infected therewith. The infected leaf disc was put on a sterilized filter paper to remove any extra cell suspension. Then, it was laid on hormone-free MS agar culture medium (T. Murashige and F. Skoog, *Physiol, Plant.*, vol.15, p.473, 1962 (provided that 0.8 w/v % agar was added thereto)) containing 50 mg/liter of acetosyringone with the back of the leaf facing upward, and was cultivated for 3 days, at 25° C. in full light (cultivation of an explant, a plant tissue and a plant were conducted under these temperature and lightening conditions unless otherwise instructed). The thus-cultivated leaf disc was then transplanted into hormone-free MS agar culture medium containing only 500 mg/liter of carbenicillin, and the cultivation was continued. As a result, 22 adventitious shoots were redifferentiated. These adventitious shoots were separated and further cultivated in a culture medium having the above-mentioned composition to obtain 6 ESP lines. These ESP lines were subcultured in the same culture medium every month, and were subcultured in hormone-free MS agar culture medium not containing carbenicillin several times 3 months after an infection. After the proliferation of Agrobacterium was not observed, a test for kanamycin resistance and PCR analysis were carried out.

IV. Analysis of a tobacco into which the gene has been introduced

A. Test for kanamycin resistance

The 6 ESP lines obtained in the above-described step III were cultivated as such without subculture. Leaves developed from these ESP lines were cut out to form leaf discs of approximately 3 mm square. The thus-obtained leaf discs were laid on MS agar culture medium (1 mg/liter of benzyl adenine and 0.2 mg/liter of α-naphthalene acetic acid were added thereto) containing 200 mg/liter of kanamycin. After cultivation in this kanamycin containing culture medium for 1 month, the formation of ESP lines was also observed on the leaf discs obtained from these ESP lines.

B. PCR analysis

Chromosomal DNAs were extracted from all of the 6 ESP lines obtained in the above-described step III, and the genes introduced thereinto were analyzed by the PCR method.

The chromosomal DNA was extracted by using the following modified CTAB method.

First, approximately 1 g of the leaves developed from the ESP was ground in liquid nitrogen using a chilled mortar and pestle, and suspended in 5 ml of a buffer (containing 2 w/v % CTAB (hexadecyltrimethylammonium bromide), 1.4-M NaCl, 0.2 v/v % β-mercaptoethanol, 20-mM EDTA, and 100-mM Tris-HCl (pH 8.0)) which has been heated at 60° C. This suspension was heated at 60° C. for from 30 to 60 minutes while being gently shaken, and was then cooled to room temperature. To this suspension a mixture of chloroform and isoamyl alcohol (24:1) at an equal volume was added, and these were gently mixed. Then, the mixture was centrifuged at 1,600×g for 5 minutes to recover a supernatant. Subsequently, ⅔ volume of isopropyl alcohol was added to the supernatant, and these were gently mixed again. The mixture was allowed to stand on ice for 10 minutes to precipitate the chromosomal DNA. This chromosomal DNA was collected by centrifugation at 1,600×g for 10 minutes. The thus-collected chromosomal DNA was washed with 70 v/v % ethanol, then vacuum-dried, and dissolved in 300 μl of TE (comprising 10-mM Tris-HCl and 1-mM EDTA).

Meanwhile, in order to detect the ipt gene by the PCR method, a couple of primers (oligonucleotide) to be used was synthesized by a DNA synthesizer (manufactured by Applied Biosystems Co.). When they were binding to the ipt gene the distance between the two primers became approximately 800 bp. To amplify the ipt gene, 1 μg of the extracted chromosomal DNA was dissolved in 50 μl of a mixed solution containing 0.2 μM of these primers 10-mM Tris-HCl (pH of 8.8 at 25° C.), 50-mM KCl, 1.5-mM MgCl$_2$, 1 w/v % Triton X-100, 0.1-mM dNTP and 1.25 units of Taq polymerase (obtained from CETUS CO.). After the mixture was heated at 94° C. for 1.5 minutes, a three-part heating cycle, namely at 94° C. for 1 minute, at 55° C. for 2 minutes and at 72° C. for 3 minutes was repeated for a total of 30 times to complete the reaction. The obtained reaction mixture was analyzed by agarose gel electrophoresis to detect the presence of the ipt gene in the chromosomal DNA by the amplification of the gene of approximately 800 bp.

Figure 6:
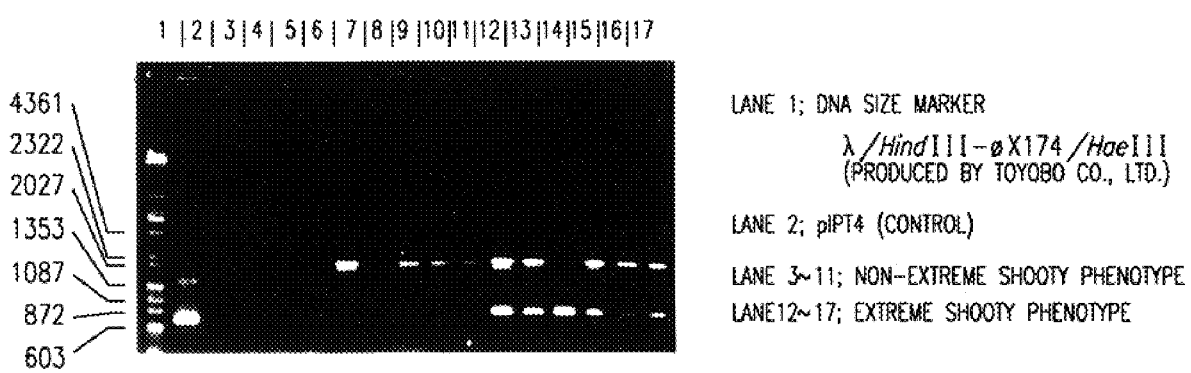
FIG. 6 is the results of PCR analysis of an extreme shooty phenotype of a tobacco into which a gene has been introduced using pIPT4.

The results are shown in FIG. 6. As is clear from FIG. 6, the amplification of the gene of approximately 800 bp was observed in all of the 6 ESPs. In FIG. 6, the values shown on the left side indicate the length of bases, which was of band ingredients detected (hereafter referred to as the "band") in the electrophoresis of the DNA size marker.

Comparative Example 1

The analysis was conducted with respect to 16 shoots which had no ability of forming an ESP and were obtained from the adventitious shoots redifferentiated from the *A. tumefaciens*-infected leaf in step III of Example 1. That is, at the time the 22 adventitious shoots were cultivated and the 6 ESP lines were selected in step III of Example 1, those showing morphologically normal shoots (hereinafter referred to as "non-ESP") were also freed from *A. tumefaciens* and subjected to the test for kanamycin resistance in the same manner as in steps III and IV of Example 1. Further, the 9 non-ESP lines were subjected to PCR analysis. However, with respect to these non-ESP lines, the leaf discs laid on the kanamycin-containing culture medium all turned brown and withered after approximately 3 months. Further, in the PCR analysis, amplification of a DNA fragment of approximately 800 bp which proves the presence of the ipt gene was not detected in any of the analyzed nine lines.

The results of the PCR analysis are shown in FIG. 6.

Example 2

I. Construction of a vector

Plasmid pHSG398 (obtained from Takara Shuzo Co., Ltd.) was digested with restriction endonuclease BamHI. The cohesive termini produced by the digestion were changed into blunt-ended termini with T4DNA polymerase I (large subunit), and plasmid pNPI100 was obtained by ligating these termini. That is, the pNPI100 was the pHSG398 losing the BamHI restriction endonuclease site. Meanwhile, plasmid pCKR97 (T. Izawa et al., *Mol. Gen. Genet.*, vol.227, p.391, 1991) was digested with restriction endonuclease PstI. Transposon Ac of a maize was cut out, and inserted into the PstI restriction endonuclease site of the pNPI100 to obtain plasmid pNPI102.

Subsequently, from the plasmid pIPT4 constructed in Example 1, a cauliflower mosaic virus 35S promoter and an ipt gene linked thereto were cut out with restriction endonucleases HindIII and SacI. The cohesive termini of the thus-obtained fragment were changed into blunt-ended termini with T4DNA polymerase I, and the fragment was inserted into the HincII restriction endonuclease site of the plasmid pUC119 to obtain plasmid pNPI101. From this plasmid pNPI101, the cauliflower mosaic virus 353S promoter and the ipt gene were cut out again with restriction endonucleases PstI and EcoRI, and the cohesive termini of the fragment were changed into blunt-ended termini with T4DNA polymerase I. Further, plasmid pNPI103 was obtained by ligating the fragment into the blunt-ended BamHI endonuclease site of pNPI102. That is, in the plasmid pNPI103, the 35S promoter and the ipt gene linked thereto existed in the old BamHI restriction endonuclease site within transposon Ac.

The desired vector was obtained by cutting out transposon Ac containing the cauliflower mosaic virus 35S promoter and the ipt gene from the plasmid pNPI103 with restriction endonuclease PstI, and inserting this transposon Ac into the SseI restriction endonuclease site of vector plasmid pBI121. This was designated as plasmid pNPI103 with restriction endonuclease PstI, and inserting this transposon Ac into the SseI restriction endonuclease site of vector plasmid pBI121. This was designated as plasmid pNPI106.

This plasmid pNPI106 was also introduced in *E. coli* JM109 strain, and it was deposited in accordance with the Budapest Treaty as *E. coli* JM109 (pNPI106) under Deposit No. FERM BP-5064.

Figure 7:
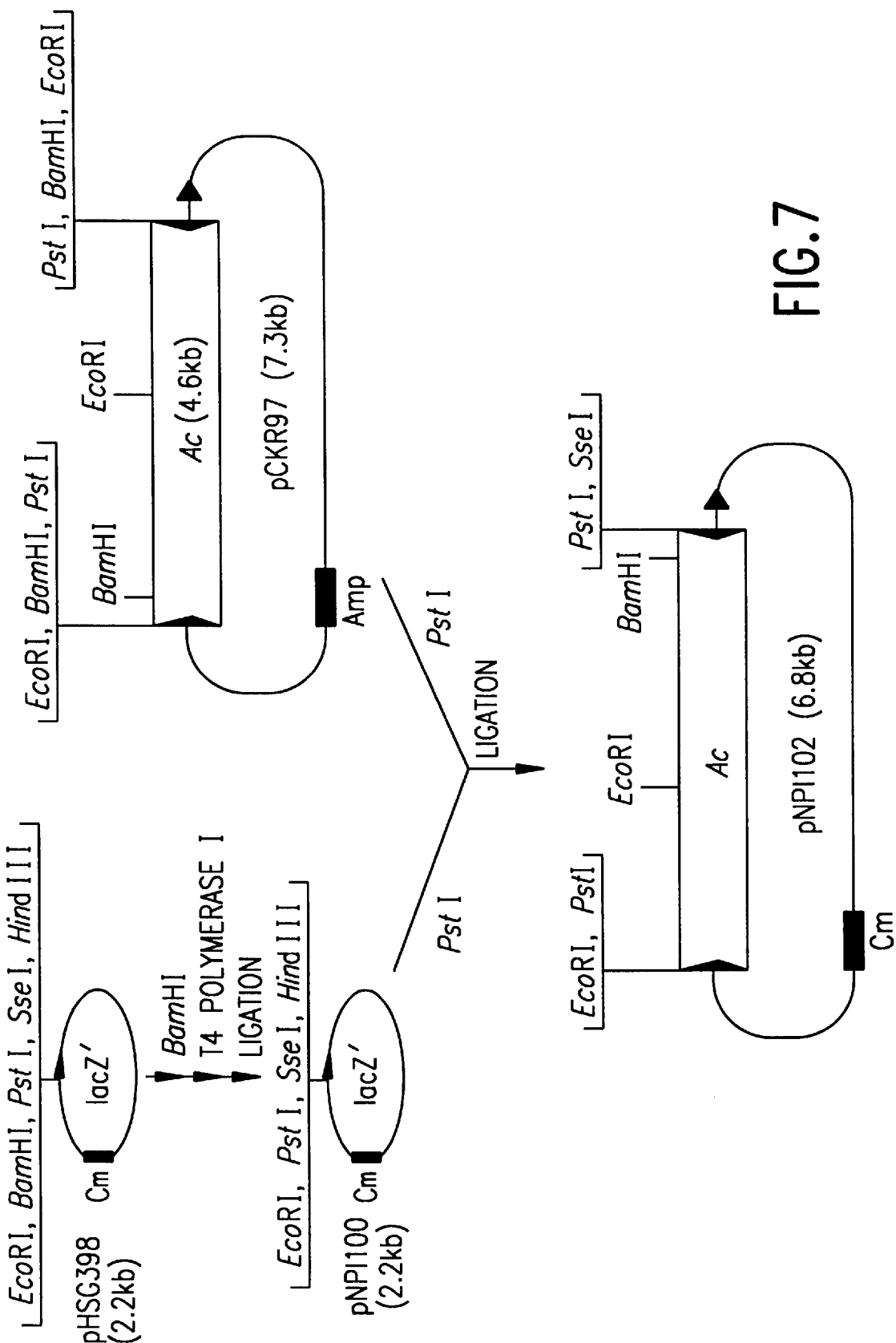
FIG. 7 is a diagram of the construction of pNPI102.
Figure 8:
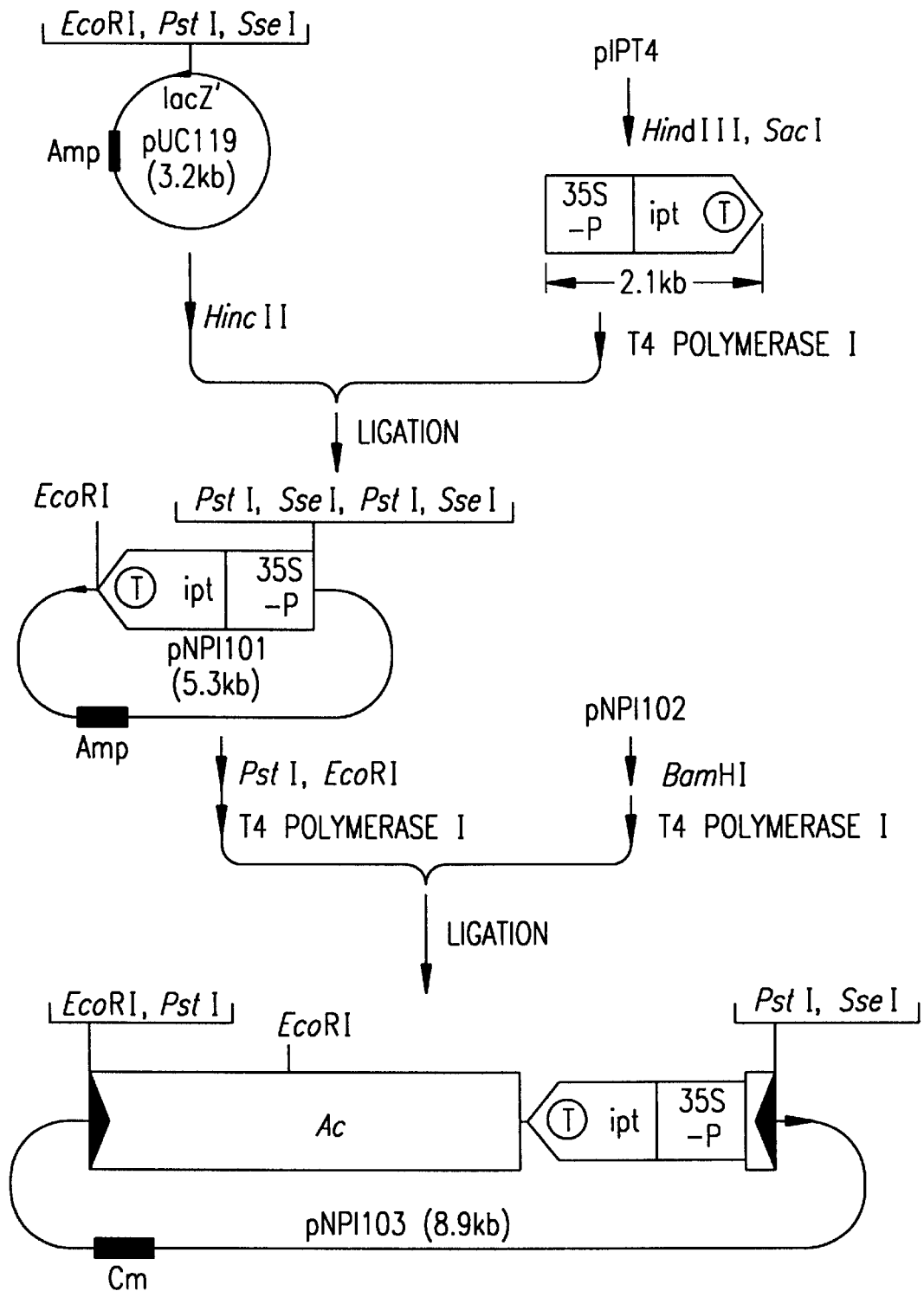
FIG. 8 is a diagram of the construction of pNPI103 from pIPT4 and pNPI102.
Figure 9:
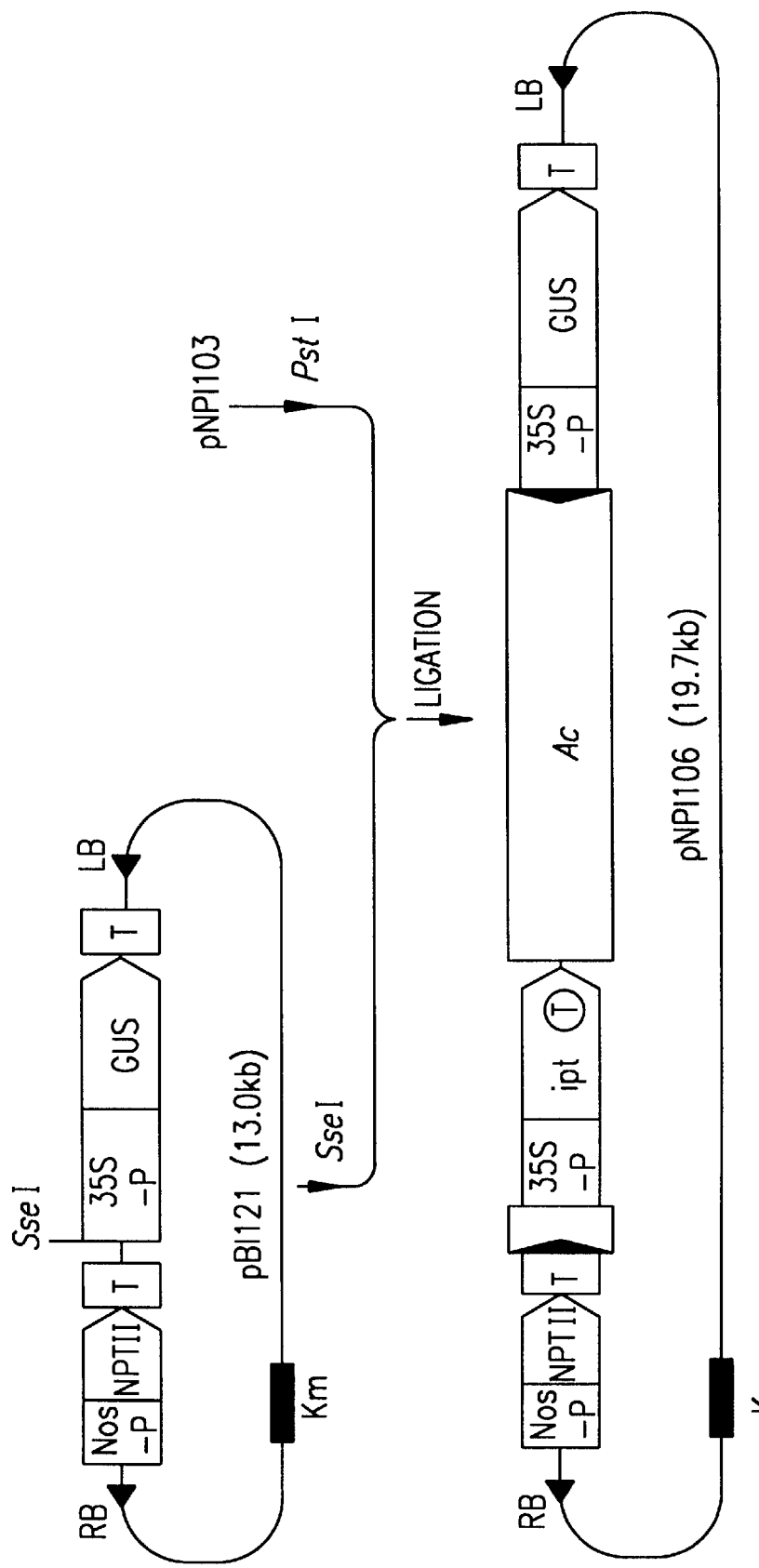
FIG. 9 is a diagram of the construction of pNPI106 from pNPI103.
Figure 10:
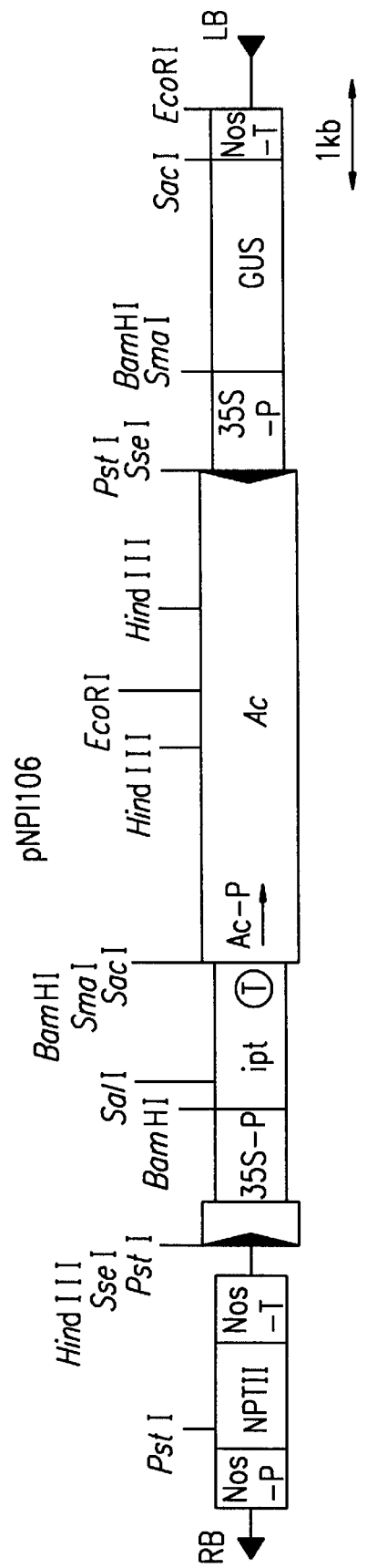
FIG. 10 is the restriction endonuclease map of a T-DNA region in the structure of pNPI106.

The strategy for constructing the plasmid pNPI106 is schematically shown in FIGS. 7 to 9. A restriction endonuclease map of the T-DNA region thereof is shown in FIG. 10. In FIGS. 7 to 9 and 10, the terminal region of transposon Ac is shown by opposite black triangles, respectively. In FIG. 10, Ac-P is a native promoter present within Ac. Other symbols are the same as those shown in FIGS. 2 to 5.

As is clear from FIG. 10, this plasmid has the ipt gene as the marker gene, and the NPTII gene and GUS (β-galactosidase) gene as a model of the desired gene in the T-DNA region, namely in the region to be integrated into the chromosome of the plant. Further, the ipt gene is present as inserted within the transposon Ac. Since the cell having the GUS gene metabolizes a special substrate to produce a blue pigment, the expression of the gene can be identified by detecting this pigment. Thus, the GUS gene is often used for analysis of the expression of the gene in the plant.

II. Introduction of pNPI106 into a tobacco and analysis of a tobacco into which the gene has been introduced A. Introduction of pNPI106 into a tobacco and test for expression of the introduced gene In the same manner as in step II and III of Example 1, pNPI106 was introduced into *A. tumefaciens* strain LBA4404, and leaf discs of tobacco were infected with this *A. tumefaciens*. The thus-infected tobacco leaf was cultivated in hormone-free MS agar culture medium containing 50 mg/liter of acetosyringone, and then in the hormone-free MS agar culture medium to which 500 mg/liter of carbenicillin. After two months of such cultivation, 63 ESP lines were separated.

These ESP lines were transplanted in the culture medium of the same composition (hormone-free MS agar culture medium containing 500 mg/liter of carbenicillin). One month later, from among the shoots of the ESPs which had grown slightly, 9 shoots (those which are generated from ESPs are called simply "shoots" hereinafter) were selected visually which had grown approximately two or more times in comparison to the other shoots, in which the growth of the side shoots was not observed and in which the influence of the ipt gene appeared to be decreased. The leaves of those shoots were subjected to the same test for kanamycin resistance as conducted in step IV-A of Example 1 and the test for the expression of the GUS gene (test for GUS activity) based on the method of Jefferson et al. The shoots obtained after the leaves were cut off were transplanted in hormone-free MS agar culture medium and cultivated. One month later, the shapes were observed to detect the ability of forming the ESPs of the shoots, thus exhibiting, the expression of the ipt gene.

The results are shown in Table 1.

TABLE 1

Results of a test for expression of a gene introduced into a tobacco by vector pNPI106

|  | Shoot No. | Kanamycin resistance | GUS activity | Morphology after 1 month of cultivation |
|---|---|---|---|---|
| Example 2 | 1 | + | + | ESP |
|  | 2 | + | + | ESP |
|  | 3 | + | − | ESP |
|  | 4 | + | + | ESP |
|  | 5 | + | − | ESP |
|  | 6 | + | − | ESP |
|  | 7 | + | + | ESP |
|  | 8 | + | + | normal |
|  | 9 | + | + | ESP |
| Comparative | 10 | − | − | normal |
| Example 2 | 11 | − | − | normal |
|  | 12 | − | − | normal |

Notes:
1. In the kanamycin resistance, + is "resistant", and − is "not resistant".
2. In the GUS activity, + is "active", and − is "inactive".
3. The "normal" means an individual that causes the dominant growth of an apical shoot and the formation of roots.

As is apparent from Table 1, although the leaf of shoot No. 8 has kanamycin resistance and GUS activity, an ESP is not formed even if the shoot is cultivated for 1 month. This is presumably because the ipt gene that causes the formation of the ESP is present in the inserted form within the transposon Ac in the plasmid pNPI106. That is, the pit gene, which is introduced into the chromosome of the tobacco by the infection with the *A. tumefaciens* containing this plasmid to the tissue and expressed at the initial stage of the tissue cultivation just after the infection, is removed together with Ac through the action of Ac during the subsequent cultivation. Meanwhile, in the same vector, the NPTII gene and the GUS gene are inserted into a position where they do not behave integrally with Ac, so that these genes still remain in the plant chromosome and are expressed.

In Table 1, although kanamycin resistance and ESP-forming ability are observed in shoots Nos. 3, 5 and 6, only the GUS activity is negative. This means that in these shoots only the GUS gene of the genes introduced by using the pNPI106 is not expressed. This is considered to be owing to the erroneous integration that occurred when these genes were integrated into the plant chromosome containing the plasmid which has the structure of pNPI106 or the like. That is, when the gene is introduced via *A. tumefaciens*, the T-DNA region, namely, the overall inner region between the RB site and the LB site must be normally integrated into the plant chromosome. However, this region is sometimes not completely integrated, but is torn and the deficient piece lacking some portion of the LB terminals is inserted. In the T-DNA region of the pNPI106, the GUS gene is present in the closest position to the LB site. Accordingly, it is considered that due to the erroneous integration in the gene introduction, the GUS gene is integrated into the chromosome in a condition which the GUS gene is torn to pieces and its own function is lost, or the GUS gene is not at all inserted thereinto, so that the GUS gene is not expressed in these shoots and the activity thereof if not observed.

Figure 11:
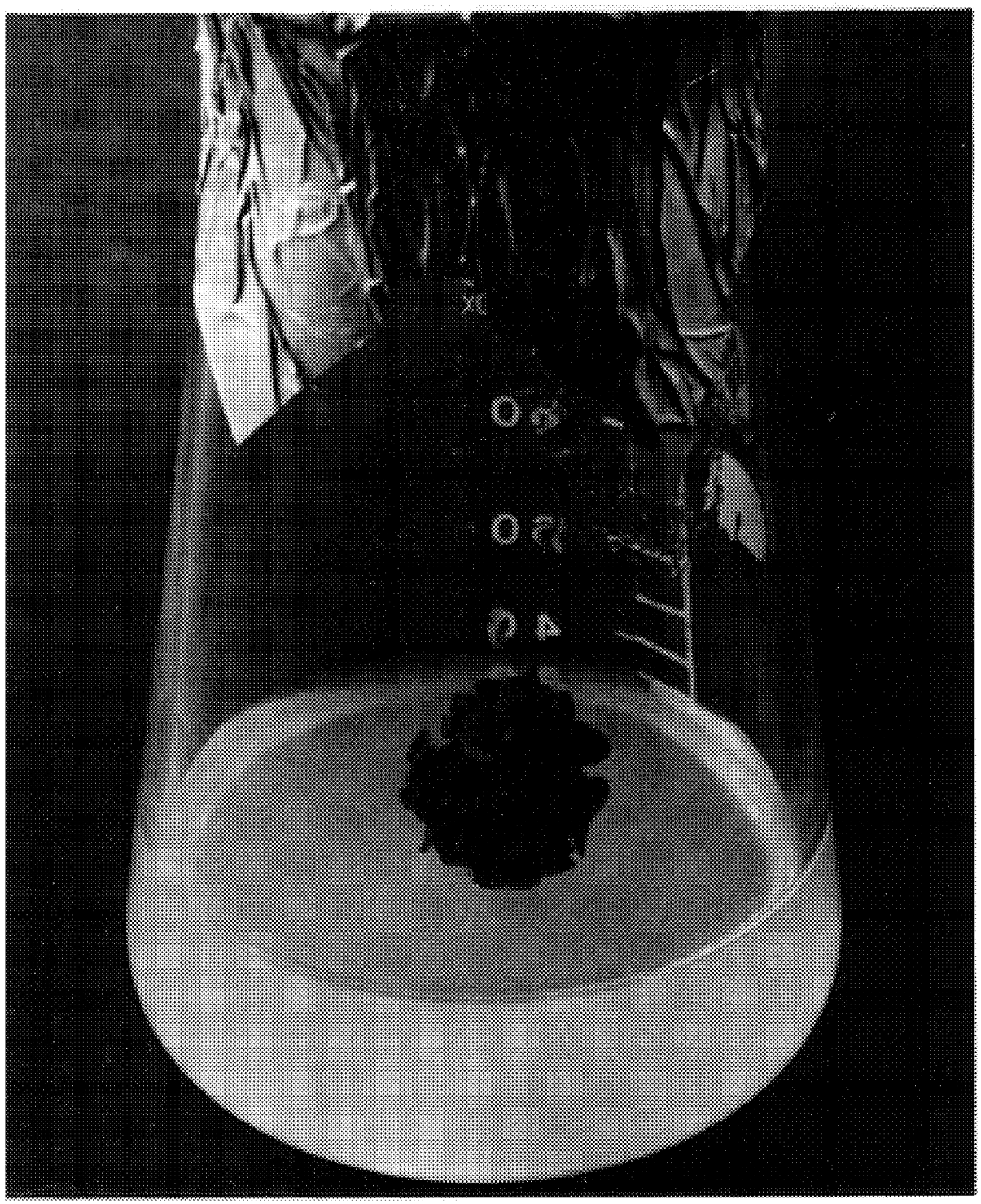
FIG. 11 is a photograph of shoot No. 2 after one month of cultivation in Example 2.
Figure 12:
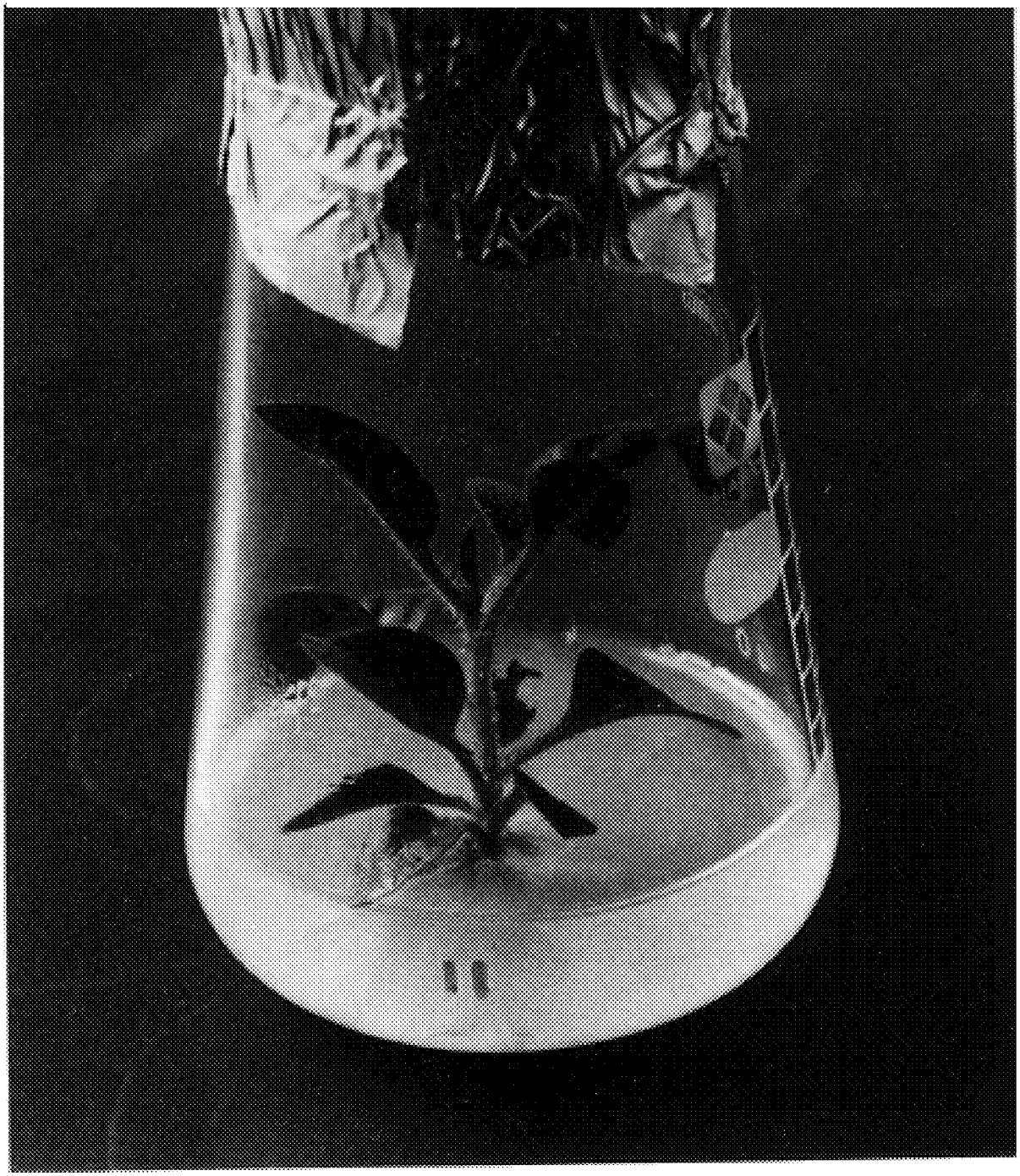
FIG. 12 is a photograph of shoot No. 8 after one month of cultivation in Example 2.

The photograph of shoot No. 2 and No. 8 after one month of cultivation are shown in FIGS. 11 and 12.

With respect to the leaf grown from shoot No. 8 and subjected to the test for kanamycin resistance here, the cultivation was further continued after the test. Five adventitious shoots were obtained from this leaf, and these were all non-ESPs.

B. PCR analysis

On shoots Nos. 1 to 9 in Table 1, after ESP-forming ability was observed, the PCR analysis was conducted in the same manner as in step IV-B of Example 1 to further examine the presence of the ipt gene in the chromosome, provided that the couple of primers which were designed to be bound to the NPTII gene and the GUS gene respectively were used in addition to the primers used in step IV-B of Example 1. In the case that these primers were used, when the Ac and the ipt gene inserted thereinto (Ac-ipt gene complex) are excised from the T-DNA region of the pNPI106, a DNA fragment of approximately 3 kb is amplified in the PCR. Accordingly, the excision of the Ac-pit gene complex from the DNA can be detected using this amplification as an index.

Figure 13:
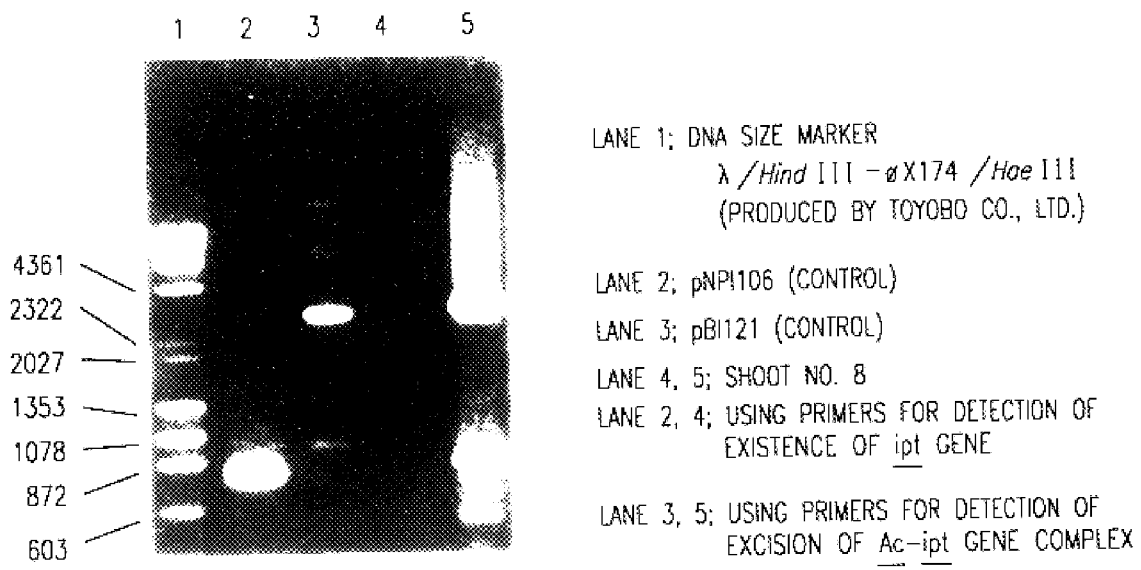
FIG. 13 is the results of the PCR analysis of shoot No. 8 in Example 2.

The results of the PCR analysis on shoot No. 8 are shown in FIG. 13, in which the values indicated on the left side are the same as those shown in FIG. 6.

As is apparent from the results, in the chromosomal DNA extracted from shoot No. 8, the amplification of the DNA fragment of approximately 3 kb which proves the excision of the Ac-ipt gene complex is observed, while the amplification of the DNA fragment of approximately 800 bp which proves the presence of the ipt gene is not observed. This means that the ipt gene is excised from the chromosomal DNA of this shoot together with the Ac and disappears.

On the other hand, with respect to shoots Nos. 1 to 7 and 9, the amplification of the DNA fragment of approximately 3 kb was not detected in any of the chromosomal DNA samples thereof, while the amplification of the DNA fragment of approximately 800 bp was detected in all of the chromosomal DNA samples thereof. Accordingly, it is considered that in these shoots, the ipt gene is still present in the chromosomal DNA along with the Ac.

COMPARATIVE EXAMPLE 2

In the cultivation of the *A tumefaciens*-infected leaf in step II-A of Example 2, the 3 non-ESPs redifferentiated along with the ESPs were separated, and subjected to the test for kanamycin resistance, the test for GUS activity, visual observation after 1 month of cultivation and PCR analysis in the same manner as in II of Example 2.

The results are shown in Table 1. The shoots obtained from these non-ESPs did not possess any of the kanamycin resistance, the GUS activity and ESP-forming ability. Besides, the amplification of the DNA fragments of approximately 800 bp and approximately 3 kb was not detected in the PCR analysis.

EXAMPLE 3

Figure 14:
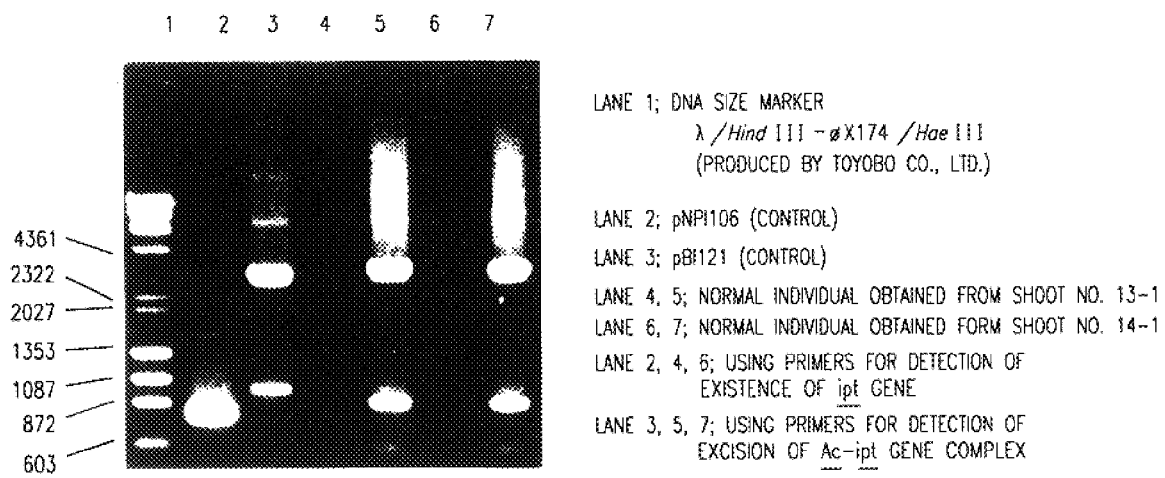
FIG. 14 is the results of the PCR analysis of normal individuals obtained from shoots Nos. 13-1 and 14-1 in Example 3.

Further, the cultivation of the 63 ESP lines separated in Example 2 were continued in hormone-free MS agar culture medium. Approximately two months later after the separation, a total of seven shoots Nos. 13-1 to 13-3 and 14-1 to 14-4 which were normal shoots capable of being identified visually, that is, which exhibited the apical dominance, were obtained from the 2 ESP lines. These shoots were separated to transplant in the culture medium having the above-mentioned composition, then they were normally extended and rooted. Of these, the individuals obtained from shoots Nos. 13-1 and 14-1 were subjected to PCR analysis in the same manner as in step II-B of Example 2. As a result, the amplification of a DNA fragment of approximately 800 bp was observed in neither shoot Nos. 13-1 nor 14-1. Meanwhile, the amplification of a DNA fragment of approximately 3 kb was observed in both of these shoots. It was thus determined that the ipt gene had been excised from the chromosomal DNA of these individuals along with the Ac and had disappeared. The results are shown in FIG. 14, in which the values indicated on the left side are the same as those shown in FIG. 6. Further, the expression of the GUS gene was detected in all of the individuals obtained from the seven shoots.

Figure 15:
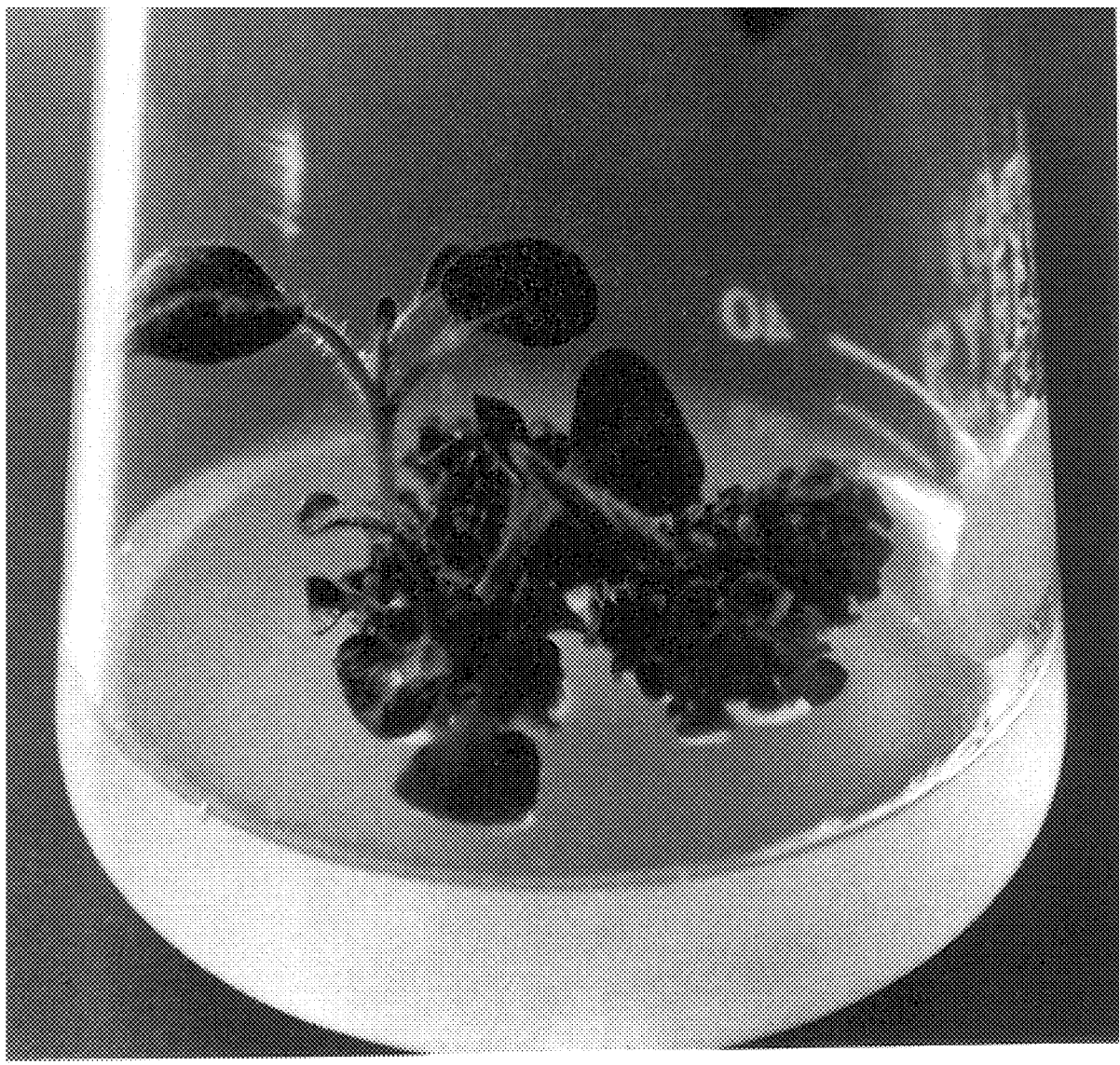
FIG. 15 is a photograph of normal shoots differentiated from an extreme shooty phenotype of a tobacco in Example 3.

FIG. 15 shows the state of a normal shoot differentiated from an ESP.

EXAMPLE 4

Figure 16:
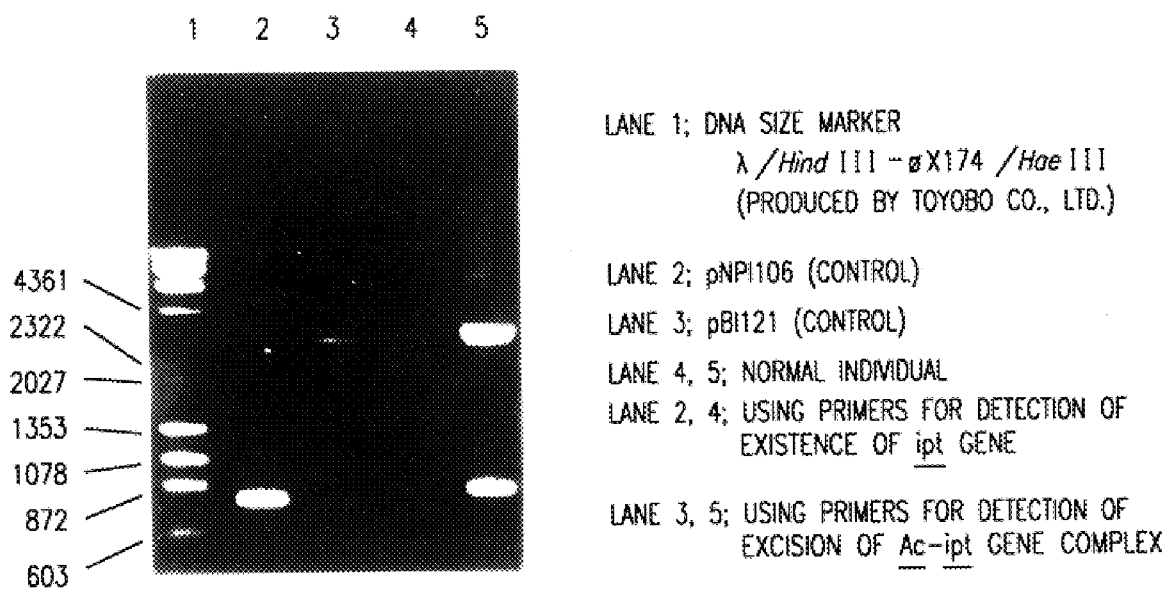
FIG. 16 is the results of the PCR analysis of a normal individual which is obtained from a leaf formed from shoot No. 7 in Example 2.

The leaf obtained from a shoot which is shown as shoot No. 7 in Table 1 among the 9 shoots selected in Example 2 was cultivated in hormone-free Ms agar culture medium for approximately 1 month. One normal shoot was visually selected and separated from 6 adventitious shoots which were redifferentiated from the cultivated leaf. This normal shoot was transplanted in a culture medium of the above-mentioned composition, then a normal extended and rooted individual was obtained. Further, this individual was subjected to PCR analysis in the same manner as in step II-B of Example 2, and on the grounds of the disappearance of the DNA fragment of approximately 800 bp and the amplification of the DNA fragment of approximately 3 kb, it was determined that the ipt gene had been excised from the chromosomal DNA along with the Ac and had disappeared. The results are shown in FIG. 16, in which the values indicated on the left side are the same as those shown in FIG. 6. Furthermore, in the same individuals, the expression of the GUS gene was also detected.

EXAMPLE 5

I. Separation of a site-specific recombination system (pSR1 system) from yeast

Yeast (*Zygosaccharomyces rouxii* (obtained form Institute for Fermentation)) was inoculated in 5 ml of YPAD liquid culture medium (containing 10 g/liter of yeast extract, 20 g/liter of polypeptone, 0.4 g/liter of adenine and 20 g/liter of glucose), and was cultivated at 30° C. for 24 hours. The culture solution was centrifuged at 6,900×g for 3 minutes at 20° C. to collect the cells (hereinafter, the cells were collected under the same conditions). The obtained cells were suspended in 2 ml of a solution comprising 0.2-M Tris-HCl (pH 8.0) and 5 v/v % mercaptoethanol. The cell suspension was allowed to stand at 25° C. for 30 minutes while being gently stirred sometimes, and cells were then collected. Further, the collected cells were suspended 1 ml of a solution (pH 6.8) containing 2.5 mg/ml of Zaimolyeis-20T (obtained from SEIKAGAKU CORPORATION), 10 w/v % sorbitol and 5 w/v % $KPO_4$. The suspension was allowed to stand at 30° C. for 90 minutes, and recentrifuged to collect the cells again. The collected cells were resuspended in 1 ml of a solution containing 0.2-M NaCl, 0.1-M EDTA, 5 w/v % SDS, 50-mM Tris-HCl (pH 8.5), and 20 Proteinase K were added to be 20 mg/ml thereto. The mixed solution was allowed to stand at 60° C. for 1 hour, then returned to room temperature, and extracted with a mixture of phenol and chloroform and then with chloroform to purify. To the thus-obtained supernatant was added in an equal volume of isopropanol to precipitate chromosomal DNA and plasmid pSR1. The mixture was centrifuged at 6,900×g for 10 minutes at 4° C. to collect the DNA, and the collected DNA was washed with 70 v/v % ethanol, then vacuum-dried and dissolved in 100 μl of TE.

Using the thus-extracted DNA (the mixture of the chromosomal DNA and the plasmid pSR1) as a template, only a site-specific recombination system which was present in the plasmid pSR1 (hereinafter referred to as "pSR1 system") was amplified by the PCR method. The pSR1 system consists of an R gene which is a recombinase gene and a recombination sequence Rs, and their DNA sequences have been already determined (H. Araki et al., *J. Mol. Biol.*, vol.182, p.191, 1985). In the present invention, in order to amplify the R gene, a primer in which an XbaI restriction endonuclease site was added to a 5'-position of 22 bases, namely, 5,596th–5,617th bases in the sequence of the plasmid pSR1 (5'-CCTCTAAATGCAATTGACCAAGGATACTG-3') and a primer in which the SacI restriction endonuclease site was added to the 5'-position of 22 bases, namely, 4,126th–4,147th bases in the sequences of plasmid pSR1 (5'-CCGAGCTCTTAATCTTGTCAGGAGGAGGTGTCA-3'), were synthesized to use. On the other hand, in order to amplify Rs, two couples of primers each comprising 30 bases (a total of four types) were synthesized to use. That is, one couple was composed of a primer in which the three of 287th–316th bases of the sequence of the plasmid pSR1 replaced and an SseI restriction endonuclease site was introduced (5'-AGGATTGAGCTACTGGACGGGAATCCTGCA-3') and a primer in which the four of 690th–719th bases of the sequence of the plasmid pSR1 were replaced and the HindIII restriction endonuclease site and the XhoI restriction endonuclease site were introduced (5'-CAACTCGAGCAATCAAAGCTTCTCGTAGTC-3'). Rs to be amplified with this primer set was called "Rs1". Another couple was composed of a primer in which the three of 287th–316th bases of the sequence of the plasmid pSR1 were replaced and an XhoI restriction endonuclease site and an EcoRI restriction endonuclease site were introduced (5'-AGGATTGAGCTACTCGAGGGGAATTCTGGA-3')

and a primer in which the five of 688th–717th bases of the sequence of the plasmid pSR1 were replaced and the SseI restriction endonuclease site was introduced (5'-ACTGGACCAATCCCTGCAGGTCGTAGTCAA-3'). Rs to be amplified with this primer set was called "Rs2".

In order to amplify the R gene and the Rs's, 1 μl of the extracted DNA solution was added to every 50 μl of the mixed solution used in step IV-B of Example 1 containing 0.2 μM each primer set respectively. A three-part heating cycle, namely, at 95° C. for 30 seconds, at 55° C. for 30 seconds and at 72° C. for 1.5 minutes was repeated on the mixture for a total of 30 times. The thus-obtained reaction mixture was analyzed through agarose gel electrolysis to confirm the amplification of the R gene and the Rs's.

II. Construction of a vector

The Rs1 amplified by the PCR method was digested with restriction endonucleases PstI and XhoI, and plasmid pNPI126 was obtained by inserting this Rs1 into the PstI-XhoI restriction endonuclease sites of pSL1180 (obtained from Pharmacia Biotech Co.).

Subsequently, in order to eliminate the EcoRI restriction endonuclease site and the HindIII restriction endonuclease site of pHSG398, digestion of these restriction endonucleases, changing the digested termini into blunt-ended termini with T4 polymerase I (large subunit) and ligation of the blunt-ended termini were repeated in sequence. In this way, plasmid pNPI121 with these restriction endonuclease sites eliminated was obtained. Plasmid pNPI127 was produced by digesting the Rs2 amplified by the PCR method with restriction endonucleases XhoI and PstI, and inserting this Rs2 into the SalI-PstI restriction endonuclease sites of the plasmid pNPI121.

Plasmid pNPI128 was obtained by cutting out Rs1 from the pNPI126 with restriction endonucleases SmaI and SpeI and inserting this fragment into the SmaI-XbaI restriction endonuclease sites of the pNPI127.

The R gene amplified by the PCR method was digested with restriction endonucleases XbaI and SacI, and inserted into the XbaI-SacI restriction endonuclease sites of pHSG398. The thus-obtained plasmid was designated pNPI124.

Then, pBI221 (obtained from Clontech Co.) was digested with restriction endonuclease PstI. The digested termini were changed into blunt-ended termini and then ligated as the above-described manner. Thus, the plasmid pNPI111 with the SseI and PstI restriction endonuclease sites eliminated was obtained. Thereafter, the R gene cut out from the pNPI124 with restriction endonucleases XbaI and SacI was inserted into the XbaI-SacI restriction endonuclease sites of the pNPI111 replacing the GUS gene to produce plasmid pNPI125. Further, a cauliflower mosaic virus 35S promoter, the R gene linked to the promoter and a polyadenylation signal of nopaline synthetase were cut out with restriction endonucleases HindIII and EcoRI and inserted into the HindIII-EcoRI restriction endonuclease sites of the pNPI128 to obtain plasmid pNPI129.

pNPI101 was digested with restriction endonuclease SmaI, and a 5'-phospholylated HindIII linker (obtained from Takara Shuzo Co., Ltd.) was inserted into the digestion site to obtain plasmid pNPI122. That is, this pNPI122 is one in which the SmaI restriction endonuclease site of the pNPI101 was replaced with the HindIII restriction endonuclease site. Further, the pNPI122 was digested with restriction endonuclease PstI, and the digested termini were changed into blunt-ended termini and ligated to produce plasmid pNPI123 with the SseI and PstI restriction endonuclease sites eliminated. From this plasmid pNPI123, a cauliflower mosaic virus 35S promoter and ipt gene linked to the promoter were cut out with restriction endonuclease HindIII, and inserted into the HindIII restriction endonuclease site of the pNPI129 to obtain the plasmid pNPI130.

The desired vector was obtained by cutting out the fragment containing the ipt gene, and the R gene, the cauliflower mosaic virus 35S promoters linked to them respectively and the Rs's present on both terminals of these genes with restriction endonuclease PstI, and inserting this fragment into the SseI restriction endonuclease site of the pBI121. The thus-obtained plasmid was designated pNPI132.

This plasmid pNPI132 was also introduced into E. coli JM109 strain, and was deposited in accordance with the Budapest Treaty as E. coli JM109 (pNPI132) under Deposit No. FERM BP-5065.

Figure 17:
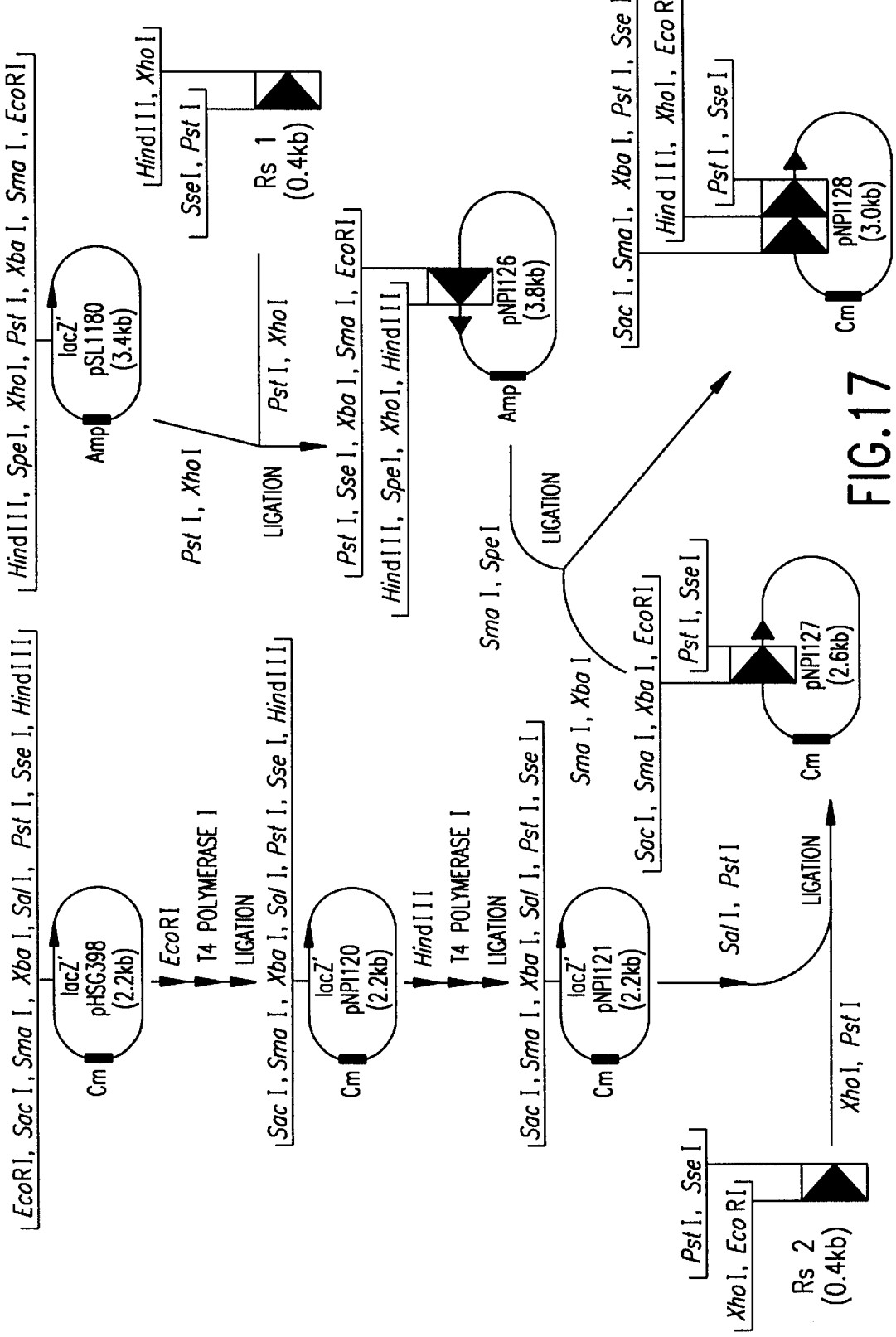
FIG. 17 is a diagram of the construction of pNPI128.
Figure 18:
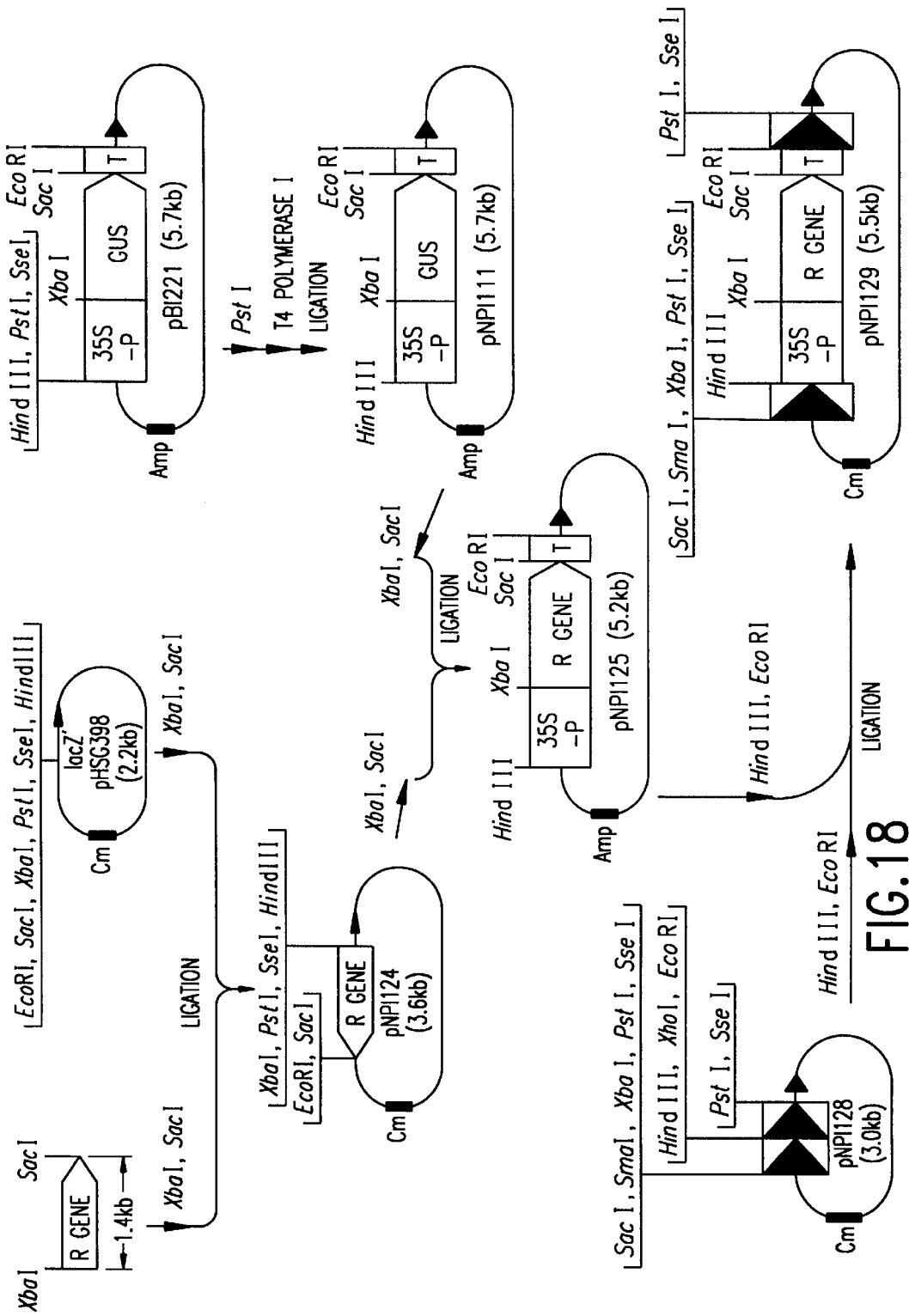
FIG. 18 is a diagram of the construction of pNPI129 from pNPI128.
Figure 19:
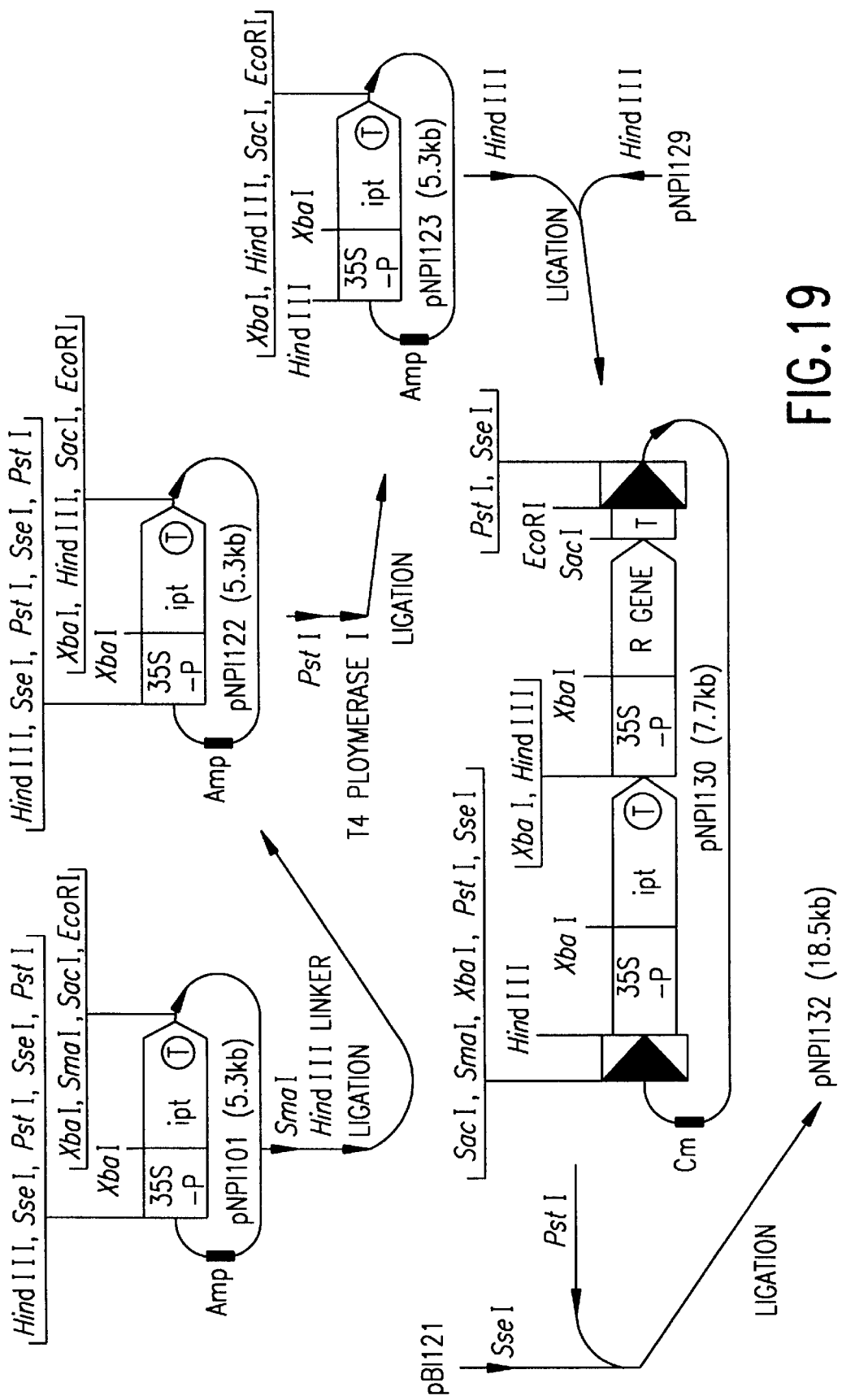
FIG. 19 is a diagram of the construction of pNPI132 from pNPI101 and pNPI129.
Figure 20:
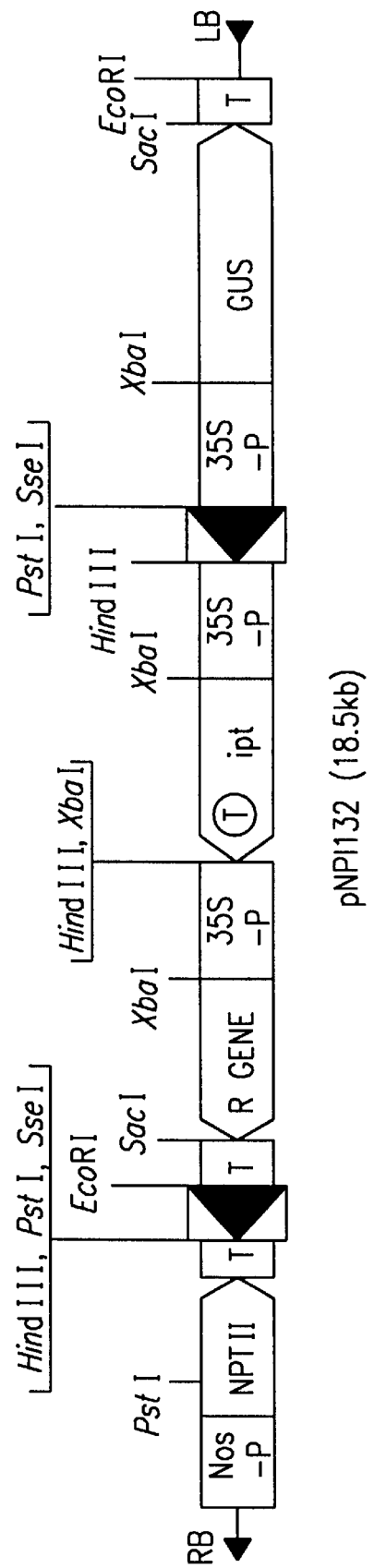
FIG. 20 is the restriction endonuclease map of the T-DNA region in the structure of pNPI132.

The strategy for constructing the plasmid pNPI132 is schematically shown in FIGS. 17–19. The restriction endonuclease map of the T-DNA region thereof is shown in FIG. 20. In FIGS. 17 to 19 and 20, a hatched triangle indicates the recombination sequence Rs derived from the plasmid pSR1 of yeast and the direction of its sequence. Other symbols are the same as those shown in FIGS. 2 to 5.

As is apparent from FIG. 20, the plasmid pNPI132, as the same as the plasmid pNPI106, has the ipt gene as the marker gene and the NPTII gene and the GUS gene as models of the desired gene in the T-DNA region. However, in this case, the region between the two recombination sequence Rs's of the pSR1 system behaves as the removable DNA element. Therefore, the ipt gene is inserted such that it is held by the two same directed recombination sequences.

III. Introduction of pNPI132 into a tobacco and analysis of the tobacco into which the gene has been introduced In the same manner as in steps II and III of Example 1, the plasmid pNPI132 was introduced into A. tumefaciens strain LBA4404, and leaf discs of a tobacco (Nicotiana tabacum cv. SR1) were infected with this A. tumefaciens. Then, the infected leaves were cultured in hormone-free MS agar culture medium containing 50 mg/liter of acetosyringone and then in hormone-free MS agar culture medium containing 500 mg/liter of carbenicillin.

One month later, the cultured leaves were transplanted in the culture medium of the same composition, and the cultivation was further continued for 1 month. Then, 48 ESP lines were separated.

These ESP lines were transplanted again in the culture medium of the same composition, and the cultivation was further continued. Approximately one month later (namely, approximately 3 months after the infection with A. tumefaciens), shoots which were visually detectable to have a normal morphology were generated from seven of 48 ESP lines. These shoots were separated and transplanted in the culture medium of the same composition, and then ten normal individuals could be obtained.

Figure 22:
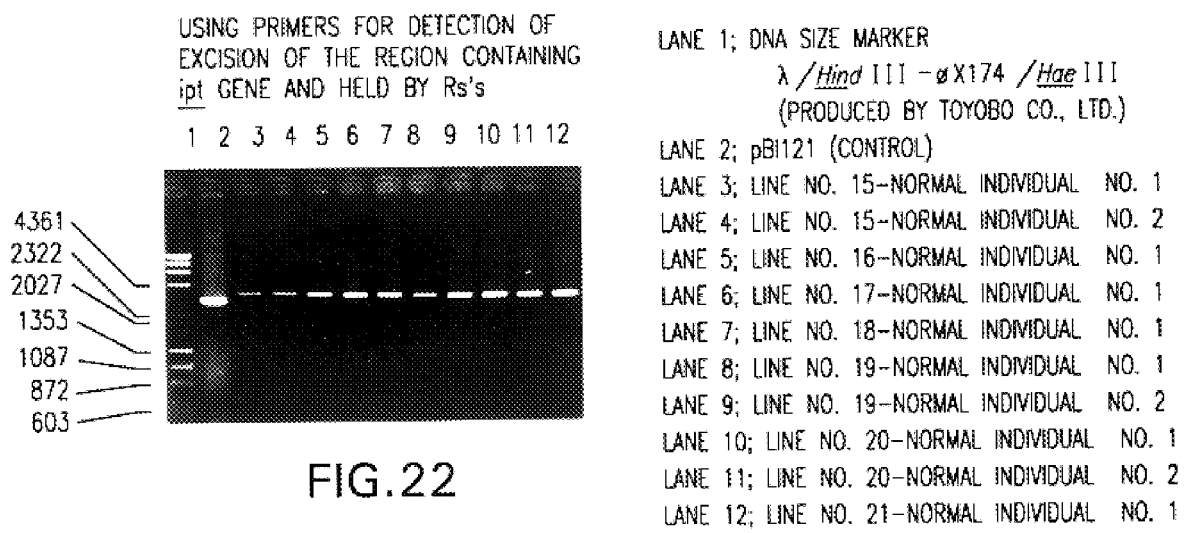
FIG. 22 is the results of the PCR analysis of normal individuals obtained from shoots Nos. 15 to 21 in Example 5 using primers in which the elimination of a region held by a couple of Rs's including an ipt gene was detected.

These individuals were subjected to the PCR analysis in the same manner as in step II-B of Example 2, provided that a couple of primers for detection of the GUS gene were used in addition to the primers used in step II-B of Example 2. By conducting PCR using these primers, a DNA fragment of approximately 800 bp was amplified when the ipt gene was present; a DNA fragment of approximately 3 kb was amplified when the ipt gene was excised from the T-DNA region of the plasmid pNPI132 through the excision of the portion held by Rs's (these results are the same as in the analysis of step II-B in Example 2); and a DNA fragment of approximately 1.7 kg was amplified when the GUS gene was present. The results are shown in FIGS. 21–23 and Table 2. The FIGS. 21–23, the values indicated on the left side are the same as those shown in FIG. 6.

TABLE 2

Results of analysis of a transgenic gene in a tobacco into which the gene is introduced with vector pNPI132

| ESP line No. | Individual plant No. | re ipt 800 bp | | re GUS 1.7 kb |
|---|---|---|---|---|
| | | | 3 kb | |
| 15 | 1 | – | + | + |
| | 2 | – | + | + |
| 16 | 1 | – | + | + |
| 17 | 1 | – | + | + |
| 18 | 1 | – | + | + |
| 19 | 1 | – | + | + |
| | 2 | – | + | + |
| 20 | 1 | – | + | + |
| | 2 | – | + | + |
| 21 | 1 | – | + | + |

Notes: + indicates that the corresponding DNA fragment is amplified, and – indicates that it is not amplified.

As is apparent from Table 2, the presence of the ipt gene which was the marker gene was not detected in any of chromosomes of the individuals that had been selected simply by the visual observation of their morphology, and instead, the amplification of the DNA fragment which indicates the excision of the ipt gene was detected. Meanwhile, the presence of the GUS gene used as the desired gene was detected in all of the individuals.

On the other hand, the kanamycin resistance was examined by using the terminal buds of individuals, which were obtained from non-ESPs differentiating almost simultaneously with the 48 ESP lines and showed normal elongation and rooting, with the use of a hormone-free MS agar medium containing 200 mg/l of kanamycin. As a result, it was found out that two among 16 individuals have resistance to kanamycin.

Figure 24A:
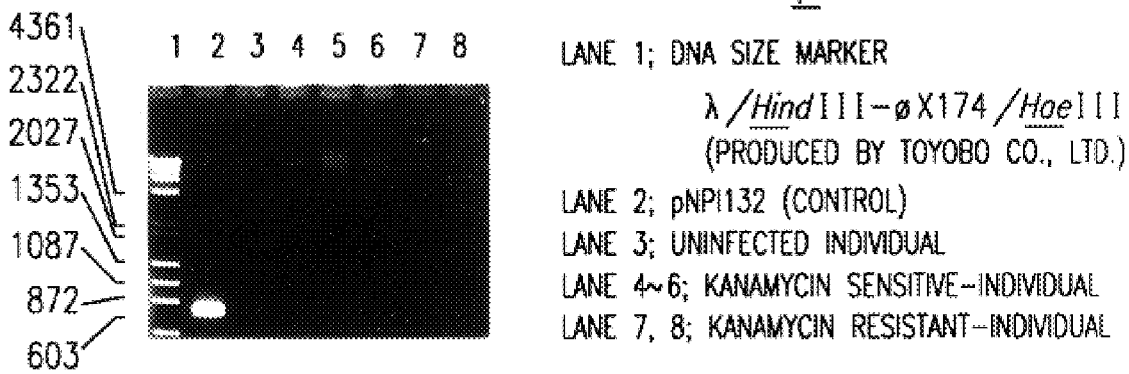
FIG. 24 is the results of the PCR analysis of normal individuals obtained from the line which could not form an extreme shooty phenotype in Example 5.
Figure 24B:
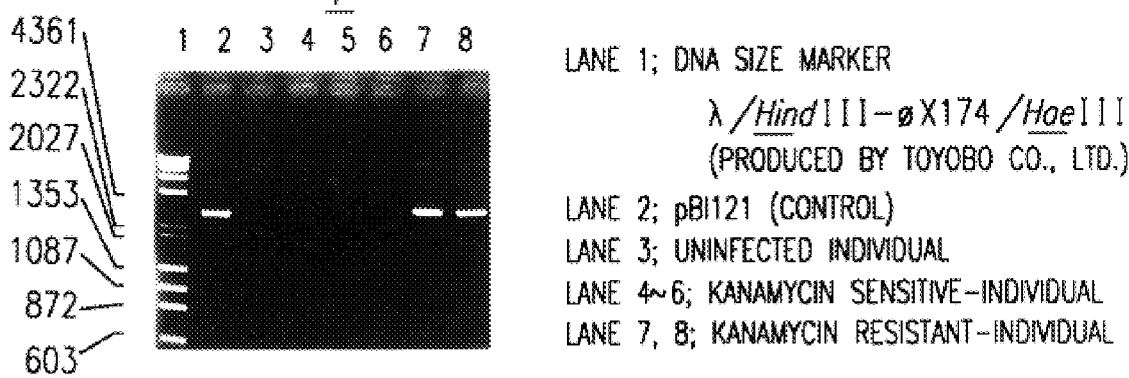
Figure 24C:
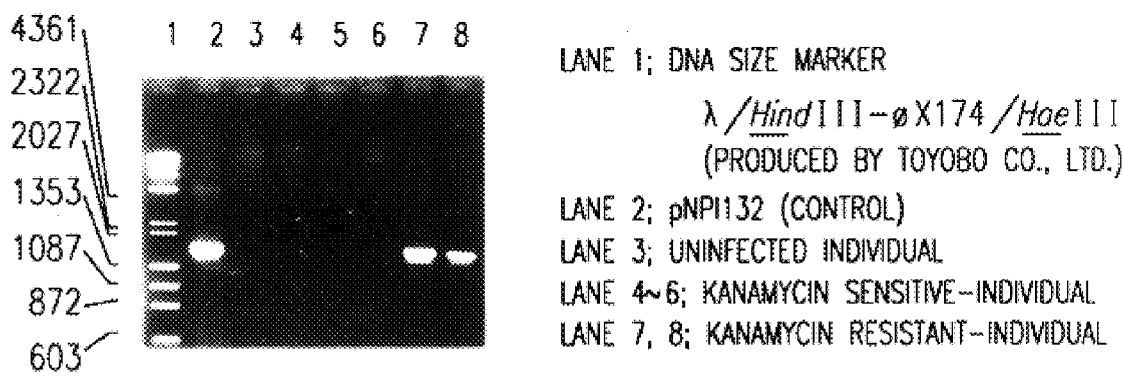

Subsequently, these kanamycin-resistant individuals were further examined by subjecting to PCR analysis together with three individuals selected among 14 kanamycin-sensitive individuals in the same manner as that employed for individuals obtained from the ESPs. FIG. 24 shows the results wherein the values indicated on the left side are have the same as those shown in FIG. 6.

As FIG. 24 clearly shows, each of the two kanamycin-resistant individuals exhibited the amplification of a DNA fragment which indicated the excision of a region containing the ipt gene and held by Rs's, and the presence of the GUS gene. Thus it was proved that genes originated in pNPI132 had been integrated into these chromosomes. In contrast, no such amplification was observed in the three kanamycin-sensitive individuals. Further, any of these individuals (namely, neither kanamycin-resistant individuals nor kanamycin-sensitive individuals) showed the amplification of a DNA fragment indicating the presence of the ipt gene.

It is assumed that these kanamycin-resistant individuals obtained from a strain lacking an ability to form ESPs, as the same as the kanamycin-sensitive individuals, originated in cells into the chromosomes of which pNPI132 had not been introduced at the infection with A. tumefaciens. Based on this assumption, it is impossible that the genes originating in this vector are contained in the chromosomes. Moreover, it is unreasonable that individuals, which lacked the ipt gene but contained the NPTII gene (as indicated by the fact that these individuals were resistant to kanamycin) and the GUS gene each in the complete form in the chromosomes, appeared at such a frequency considering all these genes originated in the same vector.

Namely, it is reasonable to conclude that, in these kanamycin-resistant individuals, pNPI132 had been once introduced into the chromosomes. That is to say, it is estimated that the T-DNA region of pNPI132 was once introduced into the chromosome due to the infection with A. tumefaciens, but the excessively efficiency function of the pSR1 system used for this vector induced the excision of the ipt gene prior to the formation of ESPs following the infection with A. tumefaciens. As a result, the NPTII gene and the GUS gene exclusively remained in the chromosome. The fact that the kanamycin-resistant individuals showed in PCR analysis, the excision of the region containing the ipt gene and held by Rs's also supports this estimation.

EXAMPLE 6

I. Construction of a vector

Rol genes (S. Kiyokawa, *Plant Physiol.*, vol.104, p.801, 1994) containing rolA, rolB and rolC and having a total size of 7.6 kb, which genes had been inserted into the EcoRI restriction endonuclease site of pBluescriptII SK+ (made by Toyobo Co., Ltd.), was cut out with a restriction endonuclease EcoRI. This fragment was inserted into the EcoRI restriction endonuclease site of the pNPI129 to produce plasmid pNPI700.

From this plasmid pNPI700, the rol genes, the cauliflower mosaic virus 35S promoter, the R gene linked to the promoter and the Rs's present on both terminals of these genes were cut out with restriction endonuclease SseI, and inserted into the SseI restriction endonuclease site of the pBI121 to obtain the desired plasmid pNPI702.

This plasmid pNPI702 was also introduced into *E. coli* JM109 strain, and was deposited in accordance with the Budapest Treaty as *E. coli* JM109 (pNPI702) under Deposition No. FERM BP-5066.

Figure 25:
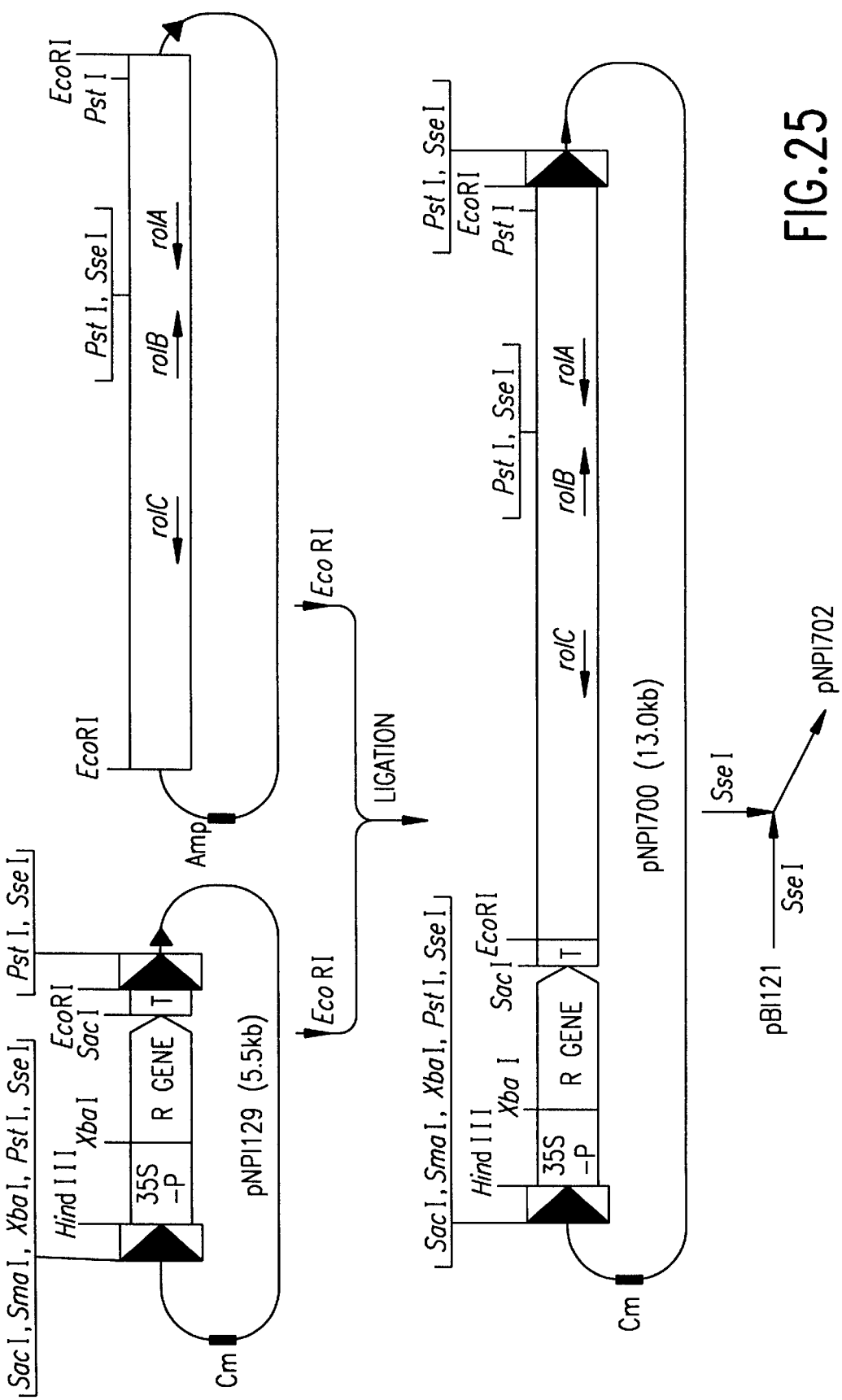
FIG. 25 is a diagram of the construction of pNPI702.
Figure 26:
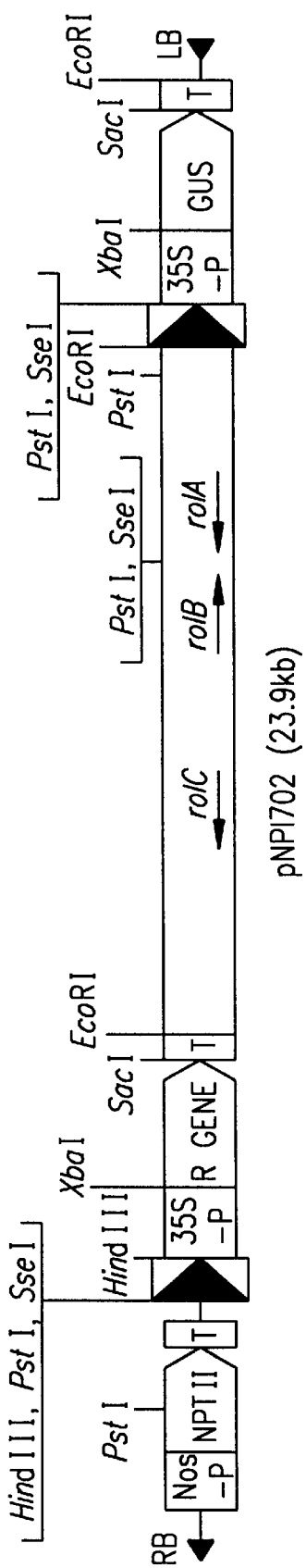
FIG. 26 is the restriction endonuclease map of the T-DNA region in the structure of pNPI702.

The strategy for constructing the plasmid pNPI702 is schematically shown in FIG. 25. The restriction endonuclease map of the T-DNA region thereof is shown in FIG. 26. The symbols in FIGS. 25 and 26 are the same as those in FIGS. 2 to 5.

As is apparent from FIG. 26, the plasmid pNPI702 is similar to the pNPI132, but only the marker gene was changed from the ipt gene to the rol genes. The rol genes used for this vector is present in the T-DNA of *A. rhizogenes* in nature. It is known that when the rol genes are introduced into plant cells, hairy roots are generated in the plant tissue and that the plant regenerated from this hairy root shows morphological abnormality such as drawfism or the like.

II. Introduction of pNPI702 into a tobacco and analysis of the tobacco into which the gene has been introduced In the same manner as in step II and III of Example 1, the plasmid pNPI702 was introduced into *A. tumefaciens* strain LBA4404, and leaf discs of a tobacco were infected with this *A. tumefaciens*.

The thus-infected tobacco leaf disc was cultivated in hormone-free MS agar culture medium containing 50 mg/liter of acetosyringone in a dark place for 3 days, and then in hormone-free MS agar culture medium to which 400 mg/liter of ticarcillin were added. Approximately 15 days later from the beginning of cultivation, differentiation of the hairy roots was observed. The hairy roots were separated one after another, laid on a shoot induction culture medium (MS agar culture medium containing 0.1 mg/liter of α-naphthaleneacetic acid, 2.0 mg/liter of benzyladenine and 400 mg/liter of ticarcillin). Then among the redifferentiated shoots, 18 shoots considered to have a normal morphology were visually selected, and subjected to the PCR analysis in the same manner as in step II-B of Example 2, using the primers for the detecting to excise the region containing the rol genes and held by Rs's through the amplification of a DNA fragment of approximately 3 kb (as the same primers used in Examples 2 to 5 and Comparative Example 2) and the primers for detection of the presence of the rol genes through the amplification of a DNA fragment of approximately 1.1 kb. As a result, it was confirmed that the region containing the rol genes and held by Rs's was excised from the chromosomes of the 9 shoots.

EXAMPLE 7

By using the vector pNPI106 constructed in the above Example 2, a hybrid aspen (*Populus Sieboldii* x *Populus grandidentata*; a woody plant) was subjected to gene introduction.

The stem of the hybrid aspen strain Y63 (harvested in the experimental forest of Akita Jujo Chemicals Co., Ltd.) grown in a sterilized flask was cut into a nod-free section of 5 mm in length. Then it was further vertically cut into two pieces to use as a sample, and the sample was infected with the pNPI106-introduced *A. tumefaciens* strain LBA4404 in the same manner as in step of Example 1. After the infection, the stem section was placed on a hormone-free modified MS agar culture medium (containing 2 w/v % sucrose and 0.8 w/v % agar) to which 40 mg/liter of acetosyringone was added and cultivated therein for 3 days. Subsequently it was transplanted into the same medium but containing 500 mg of carbenicillin instead of acetosyringone and further cultivated therein. The modified MS culture medium employed herein is one prepared by changing the concentrations of ammonia-nitrogen and nitrate-nitrogen of the usual MS culture medium respectively to 10-mM and 30-mM, respectively.

After approximately two months, the adventitious buds growing from this section were separated and further cultivated for 2 months. Thus 6 ESP lines were obtained. These strains were further subcultured, and approximately 4 months thereafter (i.e., approximately 8 months after the infection with *A. tumefaciens*), morphologically normal shoots growing from the ESPs were observed for the first time. Then these shoots were transplanted into a ⅔-diluted MS gellan gum medium (containing 2 w/v % sucrose and 0.3 w/v % gellan gum) to which 0.05 mg/liter of IBA (indolebutyric acid) were added and cultivated therein. Thus, seven normal individuals growing roots were obtained in total from the 2 EPS lines within ten months following the infection with *A. tumefaciens*.

These individuals were then subjected to the PCR analysis in the same manner as in step III of Example 5. As a result, the ipt gene was detected from none of them. On the other hand, the presence of the GUS gene was detected in two individuals among them. Thus it was confirmed that the vector of the present invention would work efficiently in a woody plant too.

Incidentally, in the remaining 5 normal individuals, only a part of the GUS gene was detected. It seems that, in such an individual, when the transposon Ac introduced by the vector pNPI106 was excised from the chromosome together with the ipt gene, the GUS gene located in the vicinity thereof was involved in the excision and thus tore off.

Figure 27:
FIG. 27 is a photograph of normal shoots differentiated from an extreme shooty phenotype of the hybrid aspen in Example 7.

FIG. 27 shows the state of a normal shoot differentiated from an ESP.

EXAMPLE 8

The normal individual (obtained via ESP) having the genes introduced thereinto by pNPI132 in Example 5 was further subjected to gene introduction with the use of the vector of the present invention.

Figure 28:
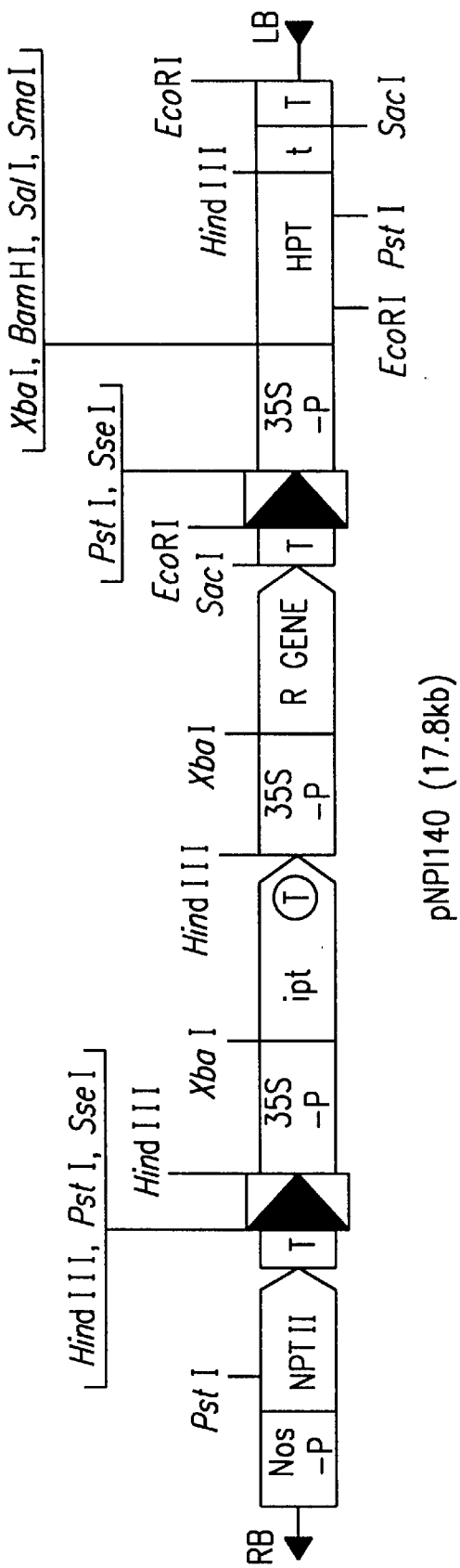
FIG. 28 is the restriction endonuclease map of the T-DNA region in the structure of pNPI140.

The GUS gene of pNPI132 was replaced by an HPT gene (hygromycin resistance gene). By using the thus-obtained vector (pNPI140, FIG. 28), the above-mentioned normal individuals were subjected to gene introduction in the same manner as in steps II and III of Example 1. Thus 10 ESP lines were obtained 40 days after the infection with *A. tumefaciens* having this vector introduced thereinto. These ESP lines were separated, transplanted into a culture medium of the same composition (hormone-free MS agar culture medium containing 500 mg/liter of carbenicillin) and further cultivated therein. As a result, the differentiation of shoots, which visually normal morphology, was observed in one of these lines 20 days thereafter (namely, approximately 2 months after the infection with *A. tumefaciens*).

One of these normal shoots thus differentiated was subjected to PCR analysis in the same manner as in steps of IV-B of Example 1. FIG. 29 shows the result. It is to be noted that a couple of primers designed to bind onto the NPTII gene and the HPT gene respectively, for detecting the excision of the region containing the ipt gene and held by Rs's, from the chromosomal DNA, and another couple of primers for detecting the presence of the HPT gene (detected through the amplification of DNA fragments of approximately 4 kb and approximately 1 kb, respectively) were employed herein in addition to the primers used in step IV-B of Example 1. In FIG. 29, the values indicated on the left side are the same as those shown in FIG. 6.

As FIG. 29 clearly shows, in the PCR analysis, the chromosomal DNA extracted from the shoot showed the amplification of the DNA fragment of approximately 4 kb, which indicated that the ipt gene had been excised through the excision of the region held by Rs's, and the amplification of the DNA fragment of approximately 1 kb, which indicated the presence of the HPT gene. On the other hand, the amplification of the DNA fragment of approximately 800 bp, which indicated the presence of the ipt gene, was not detected in the same DNA. These results suggest that the ipt gene, which had been once introduced into the chromosomal DNA of this shoot, was excised therefrom through the excision of the region held by Rs's and thus disappeared, while the HPT gene still remained in the DNA. That is to say, an individual introduced with the desired genes (i.e., the HPT gene and the GUS gene) by pNPI132 was further introduced with a novel desired gene (i.e., the HPT gene), by using a vector, wherein the construction relating to the desired gene was exclusively (i.e., the same ipt gene used as the marker gene) with repeating the cultivation, the visual selection and the separation usually. Moreover, the results showed it's quite possible that the third, fourth or more desired genes could be introduced with the use of the same marker gene.

As is apparent from the above-described Examples, the obtained ESP lines always had the ipt gene within their chromosomes as shown in FIG. 6. Further, the ESPs, which showed remarkable morphological abnormality that could be visually identified, exhibited kanamycin resistance, without exception, by the expression of the NPTII gene which was the desired gene as a model and introduced together with the ipt gene. This proves that such an MAI gene is fully available as a marker gene for introducing a gene into a plant, and that the vector of the present invention containing this MAI gene as the marker gene is also available as a vector for introducing a gene into a plant.

When a gene was introduced into a plant using the vector pNPI106 in which the ipt gene was integrated within the transposon Ac, a shoot or the like that lost its ESP-forming ability as a result of the ipt gene disappearance from the chromosome, while retaining characteristics provided by the desired gene (NPTII gene and/or GUS gene), was obtained from the tissue that once formed the ESP at the initial stage of the cultivation just after the operation of introducing the gene, as shown in Table 1 and FIGS. 13, 14 and 16. Besides, the morphology of this obtained tissue (i.e., shoot or the like that lost its ESP-forming ability) could be visually identified as shown in FIGS. 15 and 27. Further, when this was selected, separated and cultivated, an extended, and rooted individual having a normal morphology was obtained. Furthermore, tissues which were redifferentiated from the tissue obtained from the shoot that lost the ESP-forming ability also showed normal morphologies without having ESP-forming ability. This proves that such a shoot or the like consisted of uniform cells.

The same results were also observed when one derived from the site-specific recombination system was used as the removable DNA element and when the rol genes were used as the MAI gene. That is, when a gene was introduced into a plant using a vector, in which the construction relating to the transposon or the transposon and the ipt gene of the vectors used in Examples 1 to 4 and 7 was replaced with that relating to the above-mentioned recombination system and/or rol genes as described in Examples 5 and 6, the morphologically normal tissue and plant in which the MAI gene disappeared from its chromosome, while maintaining the desired gene, was obtained from the tissue that showed the abnormal morphology immediately after the gene introduction (FIGS. 21–23, Table 2). Further, it is also possible to multitudinously introduce desired genes into the same individual with repeating the steps of gene introduction, cultivation and visual selection by using the vector wherein the construction relating to the desired gene is exclusively altered while the same morphological abnormality-inducing gene is employed as the marker gene (Example 8, FIG. 29).

Accordingly, when such a vector is used, in which the MAI gene is used as the marker gene and is inserted into the position such that it behaves integrally with the removable DNA element, a tissue made only of cells in which the desired gene alone remains in the chromosome or the like and maintains its function is obtained only by conducting the following steps: (1) cultivating the cells just after the operation of introducing the gene, and visually selecting a morphologically abnormal tissue which appears during the cultivation, (2) further cultivating that morphologically abnormal tissue, and visually selecting a morphologically normal tissue which appears during the cultivation. Further, a plant made only of such cells can be also obtained from that morphologically normal tissue.

Besides, when one derived from the site-specific recombination system was used as the removable DNA element, since the excision thereof occurred quickly and quite a high frequency, the morphologically normal tissue appearing from the morphologically abnormal tissue could also be detected quickly, and many normal individuals were obtained therefrom at good efficiency.

Table 3 shows the efficiency at which the normal individual was obtained from the morphologically abnormal tissue when the transposon or one derived from the site-specific recombination system was used as the removable DNA element in the vector of the present invention.

TABLE 3

Difference in efficiency of obtaining normal individuals depending on a type of a removable DNA element:

| | Vector | Removable DNA element | Number of ESP lines | Number of lines in which normal individuals regenerate |
|---|---|---|---|---|
| Example 3 | pNPI106 | Ac (transposon) | 63 | 2 (7 individuals) |
| Example 5 | pNPI132 | the region held by Rs's of pSR1 system (site-specific recombination system) | 48 | 7 (10 individuals) |

Notes:
1. The ESP was separated after two months of the cultivation.
2. The normal shoot could be detected after four months of cultivation in Example 3 and after three months of cultivation in Example 5.
3. Each of the above-mentioned normal individuals contained a GUS gene as a model of the desired gene.

In Examples 1 to 5, under the hormone-free conditions, the tissue containing the transgenic cells proliferated, differentiated the adventitious shoot, and regenerated the plant. This is presumably ascribable to the action of the ipt gene which was introduced into the chromosome in the transgenic cell as the marker gene. That is, by the expression of this gene, the plant hormone was overproduced within the cell. Consequently, the plant hormone produced in the cell containing the ipt gene influenced not only did the cell itself to differentiate the tissue such as the ESP or the like, but also the tissue adjacent to the cell to some extent, whereby the same state as that given by the artificial addition of the plant hormone to the culture medium was created.

In the vector of the present invention, the MAI gene is used as the marker gene. Therefore, when the gene introduction is conducted on the plant using this vector, the tissue into which the desired gene is introduced may be selected by cultivating the cell subjected the treatment for the gene introduction, in a common culture medium under common cultivation conditions without adding any chemical substance for selection, and visually identifying the resulting morphologically abnormal tissue. Accordingly, the procedure is simplified, and the activity of the plant cell does not decrease during the selection.

Further, such as MAI gene is inherent in the plant or is introduced into the plant by infection with bacteria or the like in nature. For this reason, even if the MAI gene is expressed within the plant cell into which the gene has been introduced, its safety is considerably high when ingested into the human body.

Still further, when the ipt gene is used as the MAI gene, the tissue containing the transgenic cell proliferated and differentiated the adventitious shoot by the action of this gene, making it possible to eliminate the need for the addition of plant hormones to the culture medium which is generally deemed indispensable for the proliferation and differentiation in the cultivation of the plant cell.

In addition, in this vector, the MAI gene used as the marker gene is inserted into the position such that it behaves integrally with the removable DNA element, whereby the marker gene is removed from the DNA where this gene exists and functions through the excision of the DNA element at a given ratio after the gene has been introduced into the plant cell, and this loses its own function. Thus, only the desired gene present in a position of the vector such that it does not behave integrally with the removable DNA element remains in the same DNA, and maintain the ability to express its function. Accordingly, in this structure, the vector causes the multiple introduction relating to the gene into a certain plant by merely changing the portion of the desired gene to be introduced without any changing the structures of the marker gene and the others. Thus, the multiple introduction can be conducted an unlimited number of times.

Besides, in this case, the loss of the function of the MAI gene as the marker gene can be visually detected through the morphological change of the transgenic tissue as in the introduction of this gene. Therefore, tissue made up only of the cells in which the desired gene alone remains in the chromosome or the like and maintains its function can be selected surely and easily. As a result, the multiple introduction of the gene can be conducted at high efficiency, and the transgenic plant made only of such cells, namely, the individual free from the influence of the marker gene and completely free from any health risks posed by the marker gene product can be obtained without having to undergo the crossing step.

While the invention has been described in detail and with reference to specific examples thereof, it will be apparent to one skilled in the art that various changes and modifications can be made therein without departing from the spirit and scope thereof.

What is claimed is:

1. A vector for introducing a desired gene into a plant, which comprises said desired gene, at least one morphological abnormality induction gene as a marker gene, and a removable DNA element, wherein said morphological abnormality induction gene is positioned such that it behaves integrally with the removable DNA element, and wherein said desired gene is positioned such that it does not behave integrally with the removable DNA element.

2. The vector of claim 1, wherein said morphological abnormality induction gene is present within said removable DNA element.

3. The vector of claim 1, wherein said removable DNA element is a transposon.

4. The vector of claim 1, wherein said removable DNA element is derived from a site-specific recombination system.

5. The vector of claim 1, wherein said morphological abnormality induction gene is obtained from a microorganism of the genus Agrobacterium.

6. The vector of claim 1, wherein said morphological abnormality induction gene is a cytokinin synthesis gene.

7. The vector of claim 6, wherein said cytokinin synthesis gene is an ipt, isopentenyltransferase, gene which is present in the T-DNA of *Agrobacterium tumefaciens*.

8. The vector of claim 1, wherein said morphological abnormality induction gene is at least one gene selected from rol genes.

9. The vector of claim 8, wherein said rol genes are rol genes containing rolA, rolB and rolC, which are present in the T-DNA of *Agrobacterium rhizogenes*.

10. A method for producing a transgenic plant free from the influence of a marker gene, which comprises the following steps:

(A) introducing a vector into a plant cell, wherein said vector comprises a desired gene, at least one morphological abnormality induction gene as a marker gene, and a removable DNA element, wherein said morphological abnormality induction gene is positioned such that it behaves integrally with the removable DNA element, and wherein said desired gene is positioned such that it does not behave integrally with the removable DNA element, (B) culturing the plant cell obtained in (A), detecting a morphologically abnormal plant tissue which appears during the culturing, and selecting said morphologically abnormal tissue, and (C) culturing said morphologically abnormal tissue selected in (B), detecting a morphologically normal tissue which appears during the culturing, and selecting said morphologically normal tissue.

11. The method of claim 10, wherein said morphological abnormality induction gene is present within said removable DNA element.

12. The method of claim 10, wherein said removable DNA element is a transposon.

13. The method of claim 10, wherein said removable DNA element is derived from a site-specific recombination system.

14. The method of claim 10, wherein said morphological abnormality induction gene is obtained from a microorganism of the genus Agrobacterium.

15. The method of claim 10, wherein said morphological abnormality induction gene is a cytokinin synthesis gene.

16. The method of claim 15, wherein said cytokinin synthesis gene is an ipt, isopentenyltransferase, gene which is present in the T-DNA of *Agrobacterium tumefaciens*.

17. The method of claim 10, wherein said morphological abnormality induction gene is at least one gene selected from rol genes.

18. The method of claim 17, wherein said rol genes are rol genes containing genes rolA, rolB and rolC, which are present in the T-DNA of *Agrobacterium rhizogenes*.

19. A method for introducing at least two desired genes into a plant, which comprises conducting the following steps at least two times:

(A) introducing a vector into a plant cell, wherein said vector comprises a desired gene, at least one morphological abnormality induction gene as a marker gene, and a removable DNA element, wherein said morphological abnormality induction gene is positioned such that it behaves integrally with the removable DNA element, and wherein said desired gene is positioned such that is does not behave integrally with the removable DNA element, (B) culturing the plant cell obtained in (A), detecting a morphologically abnormal plant tissue which appears during the culturing, and selecting said morphologically abnormal tissue, and (C) culturing said morphologically abnormal tissue selected in (B), detecting a morphologically normal tissue which appears during the culturing, and selecting said morphologically normal tissue.

20. The method of claim 19, wherein said morphological abnormality induction gene is present within said removable DNA element.

21. The method of claim 19, wherein said removable DNA element is a transposon.

22. The method of claim 19, wherein said removable DNA element is derived from a site-specific recombination system.

23. The method of claim 19, wherein said morphological abnormality induction gene is obtained from a microorganism of the genus Agrobacterium.

24. The method of claim 19, wherein said morphological abnormality induction gene is a cytokinin synthesis gene.

25. The method of claim 24, wherein said cytokinin synthesis gene is an ipt, isopentenyltransferase, gene which is present in the T-DNA of *Agrobacterium tumefaciens*.

26. The method of claim 19, wherein said morphological abnormality induction gene is at least one gene selected from rol genes.

27. The method of claim 26, wherein said rol genes are rol genes containing rolA, rolB and rolC, which are present in the T-DNA of *Agrobacterium rhizogenes*.

28. A transgenic plant free from the influence of a marker gene produced by a method without a sexual segregation process, which comprises the following steps:

(A) introducing a vector into a plant cell, wherein said vector comprises a desired gene, at least one morphological abnormality induction gene as a marker gene, and a removable DNA element, wherein said morphological abnormality induction gene is positioned such that it behaves integrally with the removable DNA element, and wherein said desired gene is positioned such that it does not behave integrally with the removable DNA element, and wherein said vector does not contain a gene contributing to detoxification of a plant cell growth inhibitory substance as a marker gene, (B) culturing the plant cell obtained in (A), detecting a morphologically abnormal plant tissue which appears during the cultivation, and selecting said morphologically abnormal tissue, (C) cultivating said morphologically abnormal tissue selected in (B), detecting a morphologically normal tissue which appears during the culturing, and selecting said morphologically normal tissue, and (D) cultivating said morphologically normal tissue to regenerate a plant.

29. A plant containing two or more desired genes produced by a method, which comprises the following steps:

(A) introducing a vector into a plant cell, wherein said vector comprises a desired gene, at least one morphological abnormality induction gene as a marker gene, and a removable DNA element, wherein said morphological abnormality induction gene is positioned such that it behaves integrally with the removable DNA element, and wherein said desired gene is positioned such that it does not behave integrally with the removable DNA element, and wherein said vector does not contain a gene contributing to detoxification of a plant cell growth inhibitory substance as a marker gene, (B) culturing the plant cell obtained in (A), detecting a morphologically abnormal plant tissue which appears during the cultivation, and selecting said morphologically abnormal tissue, (C) cultivating said morphologically abnormal tissue selected in (B), detecting morphologically normal tissue which appears during the culturing, and selecting said morphologically normal tissue, (D) repeating steps (A) to (C) at least one time, and (E) cultivating said morphologically normal tissue to regenerate a plant.

30. A plant containing two or more desired genes produced by a method without a sexual segregation process, which comprises the following steps:

(A) introducing a vector into a plant cell, wherein said vector comprises a desired gene, at least one morphological abnormality induction gene as a marker gene, and a removable DNA element, wherein said morphological abnormality induction gene is positioned such that it behaves integrally with the removable DNA element, and wherein said desired gene is positioned such that it does not behave integrally with the removable DNA element, and wherein said vector does not contain a gene contributing to detoxification of a plant cell growth inhibitory substance as a marker gene, (B) culturing the plant cell obtained in (A), detecting a morphologically abnormal plant tissue which appears during the culturing, and selecting said morphologically abnormal tissue, (C) culturing said morphologically abnormal tissue selected in (B), detecting morphologically normal tissue which appears during the culturing, and selecting said morphologically normal tissue, (D) repeating steps (A) to (C) at least one time, and (E) culturing said morphologically normal tissue to regenerate a plant.

* * * * *